United States Patent [19]
Tanuma

[11] Patent Number: 6,143,875
[45] Date of Patent: Nov. 7, 2000

[54] ANTIBODY TO DNASE INVOLVED IN APOPTOSIS

[76] Inventor: Sei-ichi Tanuma, 2-21-8-707, Bessho, Hachioji-shi, Tokyo 192-03, Japan

[21] Appl. No.: 09/073,613

[22] Filed: May 6, 1998

Related U.S. Application Data

[62] Division of application No. 08/640,765, filed as application No. PCT/JP95/01775, Sep. 6, 1995, Pat. No. 5,821,103.

[30] Foreign Application Priority Data

Sep. 6, 1994 [JP] Japan .................................. 6-239518

[51] Int. Cl.$^7$ .......................... C07K 16/00; C12P 21/08
[52] U.S. Cl. ................................. 530/387.9; 530/388.1; 530/388.26; 530/389.1
[58] Field of Search ........................ 530/387.1, 388.1, 530/389.1, 387.9, 388.26

[56] References Cited

PUBLICATIONS

Ishida et al., Isolation and Purification of Calcium and Magnesium Dependent Endonuclease from Rat Liver Nuclei, *Biochem. Biophys. Res. Commun.*, vol. 56, No. 3, 703–710 (1974).

Peitsch et al., Characterization of the Endogenous Deoxyribonuclease Involved in Nuclear DNA Degradation During Apoptosisi Programmed Cell Death), *The EMBO Journal*, vol. 12, No. 1, 371–377 (1993).

Polzar et al., Nucleotide Sequence of a Full Length cDNA Clone Encoding the Deoxyribonuclease I from the Rat Parotid Gland, *Nucleic Acids Research*, vol. 18, No. 23, 7151 (1990).

Shiokawa et al., Endonuclease in Apoptosis, *Experimental Medicine*, vol. 11, No. 17, pp. 2370–2375 (1993).

Shiokawa et al., Identification of an Endonulcease Responsible for Apoptosis in Rat Thymocytes, *European Journal of Biochemistry*, vol. 226, No. 1, 23–30 (1994).

Stratling et al., *Ca/Mg–Dependent Endonuclease from Porcine Liver* (1984).

Tanuma et al., Multiple Forms of Nuclear Deoxyribonuclease in Rat Thymocytes, *Biochemical And Biophysical Research Communications*, vol. 203, No. 2, pp. 789–797 (Sep. 15, 1994).

Kreuder et al., Isolation, Characterization and Crystallization of Deoxyribonuclease I from Bovine and Rat Parotid Gland and Its Interaction with Rabbit Skeletal Muscle Actin, *Eur. J. Biochem.*, vol. 139, pp. 389–400 (1984).

Goding, J.W in Monoclonal Anticbodies:Principles and Practice, Academic Pres Inc. London., 1983, pp 57–97.

Nakamura et al, J. Biochem, 89(1): 143–152, 1981.

*Primary Examiner*—Patricia A. Duffy
*Attorney, Agent, or Firm*—Leydig, Voit & Mayer, Ltd.

[57] ABSTRACT

The present invention relates to novel DNases α, β and γ capable of selectively cleaving the linker sites of chromatin DNA. The present invention also relates to novel DNase γ involved in fragmentation of chromatin DNA in apoptosis. The present invention further relates to amino acid sequence of DNase γ, DNA encoding said enzyme, nucleotide sequence of said DNA, recombinant vector containing said DNA, transformant containing said recombinant vector, production method of DNase γ comprising culture of said transformant, and antibody having affinity for said DNase γ, precursor thereof and the amino acid sequence of fragments thereof. The DNase γ of the present invention takes part in the control system of apoptosis, and effectively contributes to the development of medications for the prevention, treatment and diagnosis of apoptosis-inhibitory or promotive diseases such as cancer, autoimmune diseases and viral infections. In addition, the DNases α and β of the present invention increase upon viral infection to cleave viral DNA, and are useful for the development of therapeutic agents for viral infections.

1 Claim, 11 Drawing Sheets

F I G. 5
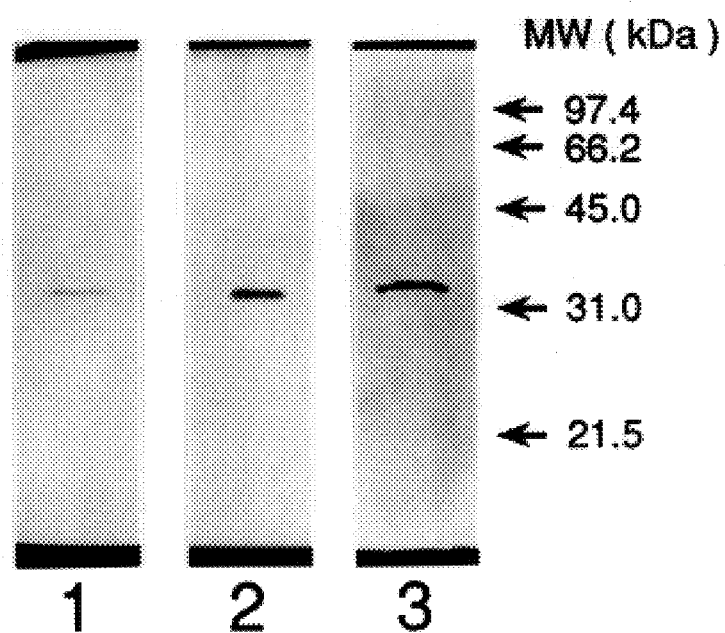

6,143,875

```
                             SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
         (A) LENGTH: 310 amino acids
         (B) TYPE: amino acid
         (C) STRANDEDNESS: single
         (D) TOPOLOGY: linear (ii) MOLECULE TYPE: protein (xi) SEQUENCE DESCRIPTION: SEQ ID NO:1:

Met Ser Leu Tyr Pro Ala Ser Pro Tyr Leu Ala Ser Leu Leu Leu Phe
                  5                  10                  15

Ile Leu Ala Leu His Gly Ala Leu Ser Leu Arg Leu Cys Ser Phe Asn
             20                  25                  30

Val Arg Ser Phe Gly Glu Ser Lys Lys Glu Asn His Asn Ala Met Asp
         35                  40                  45

Ile Ile Val Lys Ile Ile Lys Arg Cys Asp Leu Ile Leu Leu Met Glu
     50                  55                  60

Ile Lys Asp Ser Asn Asn Asn Ile Cys Pro Met Leu Met Glu Lys Leu
 65                  70                  75                  80

Asn Gly Asn Ser Arg Arg Ser Thr Thr Tyr Asn Tyr Val Ile Ser Ser
                 85                  90                  95

Arg Leu Gly Arg Asn Thr Tyr Lys Glu Gln Tyr Ala Phe Leu Tyr Lys
            100                 105                 110

Glu Lys Leu Val Ser Val Lys Ala Lys Tyr Leu Tyr His Asp Tyr Gln
        115                 120                 125

Asp Gly Asp Thr Asp Val Phe Ser Arg Glu Pro Phe Val Val Trp Phe
    130                 135                 140

Gln Ala Pro Phe Thr Ala Ala Lys Asp Phe Val Ile Val Pro Leu His
145                 150                 155                 160

Thr Thr Pro Glu Thr Ser Val Lys Glu Ile Asp Glu Leu Ala Asp Val
                165                 170                 175

Tyr Thr Asp Val Arg Arg Arg Trp Lys Ala Glu Ile Phe Ile Phe Met
            180                 185                 190

Gly Asp Phe Asn Ala Gly Cys Ser Tyr Val Pro Lys Lys Ala Trp Lys
        195                 200                 205

Asn Ile Arg Leu Arg Thr Asp Pro Asn Phe Val Trp Leu Ile Gly Asp
    210                 215                 220

Gln Glu Asp Thr Thr Val Lys Lys Ser Thr Ser Cys Ala Tyr Asp Arg
225                 230                 235                 240

Ile Val Val Arg Gly Gln Glu Ile Val Asn Ser Val Val Pro Arg Ser
                245                 250                 255

Ser Gly Val Phe Asp Phe Gln Lys Ala Tyr Glu Leu Ser Glu Glu Glu
            260                 265                 270
```

```
Ala Leu Asp Val Ser Asp His Phe Pro Val Glu Phe Lys Leu Gln Ser
        275                 280                 285

Ser Arg Ala Phe Thr Asn Ser Arg Lys Ser Val Ser Leu Lys Lys Lys
    290                 295                 300

Lys Lys Gly Ser Arg Ser
305                 310

(2) INFORMATION FOR SEQ ID NO:2:

(i) SEQUENCE CHARACTERISTICS:
        (A) LENGTH: 1208 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 12..941

(xi) SEQUENCE DESCRIPTION: SEQ ID NO:2:

CGAGTGCAAA G ATG TCC CTT TAC CCA GCT TCC CCA TAC CTG GCC TCC CTC        50
             Met Ser Leu Tyr Pro Ala Ser Pro Tyr Leu Ala Ser Leu
                  1               5                  10

CTA CTC TTC ATC CTT GCC CTT CAT GGT GCC CTG TCC CTG AGG CTC TGC        98
Leu Leu Phe Ile Leu Ala Leu His Gly Ala Leu Ser Leu Arg Leu Cys
 15                  20                  25

TCC TTC AAT GTG AGG TCC TTT GGA GAG AGC AAG AAG GAA AAC CAC AAT       146
Ser Phe Asn Val Arg Ser Phe Gly Glu Ser Lys Lys Glu Asn His Asn
 30                  35                  40                  45

GCC ATG GAT ATC ATT GTG AAG ATC ATC AAA CGC TGC GAC CTC ATA CTG       194
Ala Met Asp Ile Ile Val Lys Ile Ile Lys Arg Cys Asp Leu Ile Leu
                 50                  55                  60

CTG ATG GAA ATC AAG GAC AGC AAC AAC AAC ATC TGT CCC ATG CTG ATG       242
Leu Met Glu Ile Lys Asp Ser Asn Asn Asn Ile Cys Pro Met Leu Met
             65                  70                  75

GAG AAG CTG AAT GGA AAC TCA CGA AGA AGC ACG ACA TAC AAC TAC GTG       290
Glu Lys Leu Asn Gly Asn Ser Arg Arg Ser Thr Thr Tyr Asn Tyr Val
         80                  85                  90

ATT AGC TCT CGG CTT GGA AGA AAC ACA TAT AAA GAA CAG TAT GCC TTC       338
Ile Ser Ser Arg Leu Gly Arg Asn Thr Tyr Lys Glu Gln Tyr Ala Phe
     95                 100                 105

CTC TAC AAG GAG AAG CTG GTG TCT GTG AAG GCA AAA TAC CTC TAC CAT       386
Leu Tyr Lys Glu Lys Leu Val Ser Val Lys Ala Lys Tyr Leu Tyr His
110                 115                 120                 125

GAC TAT CAG GAT GGA GAC ACA GAC GTG TTT TCC AGG GAG CCC TTT GTG       434
Asp Tyr Gln Asp Gly Asp Thr Asp Val Phe Ser Arg Glu Pro Phe Val
                130                 135                 140

GTT TGG TTC CAG GCG CCC TTC ACT GCT GCC AAG GAC TTC GTG ATT GTC       482
Val Trp Phe Gln Ala Pro Phe Thr Ala Ala Lys Asp Phe Val Ile Val
            145                 150                 155

CCC TTG CAC ACA ACT CCT GAA ACC TCC GTT AAA GAG ATA GAT GAG CTG       530
Pro Leu His Thr Thr Pro Glu Thr Ser Val lys Glu Ile Asp Glu Leu
        160                 165                 170

GCT GAC GTC TAC ACG GAT GTT AGA AGA CGA TGG AAG GCA GAG ATT TTC       578
Ala Asp Val Tyr Thr Asp Val Arg Arg Arg Trp Lys Ala Glu Ile Phe
    175                 180                 185

ATC TTC ATG GGT GAT TTC AAT GCT GGC TGC AGC TAC GTC CCC AAG AAG       626
Ile Phe Met Gly Asp Phe Asn Ala Gly Cys Ser Tyr Val Pro Lys Lys
190                 195                 200                 205
```

```
GCC TGG AAG AAC ATC CGT TTG AGG ACA GAC CCC AAC TTT GTT TGG CTG      674
Ala Trp lys Asn Ile Arg Leu Arg Thr Asp Pro Asn Phe Val Trp Leu
                210                 215                 220

ATT GGG GAC CAA GAG GAC ACC ACG GTC AAG AAG AGC ACC AGC TGT GCC      722
Ile Gly Asp Gln Glu Asp Thr Thr Val Lys Lys Ser Thr Ser Cys Ala
                225                 230                 235

TAT GAC AGG ATT GTC GTT CGC GGA CAA GAG ATA GTC AAC TCT GTG GTT      770
Tyr Asp Arg Ile Val Val Arg Gly Gln Glu Ile Val Asn Ser Val Val
                240                 245                 250

CCC CGC TCC AGT GGC GTC TTT GAC TTT CAG AAA GCT TAT GAG TTG TCT      818
Pro Arg Ser Ser Gly Val Phe Asp Phe Gln lys Ala Tyr Glu Leu Ser
            255                 260                 265

GAA GAG GAG GCC CTG GAT GAT GTC AGT GAC CAC TTT CCA GTT GAG TTT      866
Glu Glu Glu Ala Leu Asp Val Ser Asp His Phe Pro Val Glu Phe Lys
270                 275                 280                 285

AAG CTA AGT TCA AGA GCC TTC ACC AAC AGC CGG AAA TCT GTT TCT CTA      914
Leu Gln Ser Ser Arg Ala Phe Thr Asn Ser Arg Lys Ser Val Ser Leu
                290                 295                 300

AAG AAA AAG AAA AAA GGC AGT CGC TCC TAG GTCTCATGTT GCCATTTTCT        964
Lys Lys Lys Lys Lys Gly Ser Arg Ser
                305             310

TTTCTTAAAG TCGTCCCTTG CTTCCAGATA AAATGGCCTC GTGGGTCTCA GCTCTCTGCA   1024

CACTCAGGAA TTAAGACTGG CTAAGCTGTT TTCACTGTCC ACTCTGGTTA ATTTTGCCTG   1084

GAGCCAAGTT GGGAGGAGAG CCTTCTGTTA CATCACCCTG ACCACGGGCA CCCTGCGAAC   1144

CACCATGGGT AACCTGAAGA GACACAAAGT CTATTCCATA ATAAATGCGT GTATTTATTA   1204

CCCG                                                                1208

(2) INFORMATION FOR SEQ ID NO:3:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

Leu Arg Leu Thr Ser Phe Asn Xaa Arg
                5               9

(2) INFORMATION FOR SEQ ID NO:4:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:4:

Lys Glu Asn His Asn Ala Met Asp Ile Ile Val
                5               10  11

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: single
        (D) TOPOLOGY: linear
```

-continued (ii) MOLECULE TYPE: protein (xi) SEQUENCE DESCRIPTION: SEQ ID NO:5:

Lys Glu Gln Tyr Ala Phe Leu Tyr Lys
                 5                   9

(2) INFORMATION FOR SEQ ID NO:6:

(i) SEQUENCE CHARACTERISTICS:
            (A) LENGTH: 13 amino acids
            (B) TYPE: amino acid
            (D) TOPOLOGY: linear (ii) MOLECULE TYPE: protein (xi) SEQUENCE DESCRIPTION: SEQ ID NO:6:

Lys Asp Phe Val Ile Val Pro Leu His Thr Thr Pro Glu
                 5                   10          13

(2) INFORMATION FOR SEQ ID NO:7:

(i) SEQUENCE CHARACTERISTICS:
            (A) LENGTH: 9 amino acids
            (B) TYPE: amino acid
            (D) TOPOLOGY: linear (ii) MOLECULE TYPE: protein (xi) SEQUENCE DESCRIPTION: SEQ ID NO:7:

Lys Ala Glu Asn Phe Ile Phe Met Gly
                 5                   9

(2) INFORMATION FOR SEQ ID NO:8:

(i) SEQUENCE CHARACTERISTICS:
            (A) LENGTH: 4 amino acids
            (B) TYPE: amino acid
            (D) TOPOLOGY: linear (ii) MOLECULE TYPE: protein (xi) SEQUENCE DESCRIPTION: SEQ ID NO:8:

Asp Val Phe Ser
             4

(2) INFORMATION FOR SEQ ID NO:9:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (ii) MOLECULE TYPE: other nucleic acid, synthetic DNA (xi) SEQUENCE DESCRIPTION: SEQ ID NO:9:

AARGARAAYC AYAAYGC                                                      17

(2) INFORMATION FOR SEQ ID NO:10:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: other nucleic acid, synthetic DNA (xi) SEQUENCE DESCRIPTION: SEQ ID NO:10:

```
AARGARCART AYGCNTTYYT                                                       20
```

(2) INFORMATION FOR SEQ ID NO:11:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:11:

```
AARGAYTTYG TNATHGT                                                          17
```

(2) INFORMATION FOR SEQ ID NO:12:

(i) SEQUENCE CHARACTERISTICS:
        (A) LENGTH: 11 base pairs
        (B) TYPE: nucleic acid
        (C) STRANDEDNESS: single
        (D) TOPOLOGY: linear (ii) MOLECULE TYPE: other nucleic acid, synthetic DNA (xi) SEQUENCE DESCRIPTION: SEQ ID NO:12:

```
GAYGTNTTYT C                                                                11
```

ANTIBODY TO DNASE INVOLVED IN APOPTOSIS

This patent application is a divisional of co-pending U.S. patent application Ser. No. 08/640,765, filed May 16, 1996, now U.S. Pat. No. 5,821,103, which is the U.S. national stage of International patent application PCT/JP95/01775, filed Sep. 6, 1995, which designated the United States.

TECHNICAL FIELD

The present invention relates to three kinds of novel deoxyribonucleases (hereinafter simply referred to as DNase). More particularly, the present invention relates to a novel DNase which catalyzes the fragmentation of DNA, that is, digestion of chromatin DNA into mono- or oligonucleosome units, which is a characteristic phenomenon in apoptosis.

The present invention also relates to a DNA encoding the amino acid sequence of one (DNase γ to be mentioned later) of the above-mentioned novel DNases, a vector containing said DNA, a host cell transformed with said vector, production of said DNase, which comprises culture of said host cell, and to an antibody having affinity for said DNase, a precursor polypeptide thereof or a fragment thereof.

BACKGROUND ART

Apoptosis has recently been attracting attention with regard to the death of cells or tissues. Unlike pathologic death of cells (necrosis), apoptosis is considered to be the death programmed in the gene. of cells from the beginning. That is, certain external or internal factors trigger to activate the genes which program apoptosis and the active death is brought to the cell as a result of the activation of this self-destructive program.

TABLE 1

| Phenomena of apoptosis | |
|---|---|
| [Physiological phenomena] | |
| developmental stage | morphogenesis, metamorphosis, establishment of nervous system |
| alternation of normal cells | hemocyte, epidermal cells, epithelial cells of small intestine and stomach |
| nervous system | death of neurons due to the removal of neurotrophic factors |
| endocrine | death of thymocytes by glucocorticoid atrophy of prostate by androgen removal |
| immune system | death of autoimmune cells death of tumor cells by cytotoxic T lymphocytes |
| [Pathological phenomena] | |
| irradiation | death of thymocytes highly sensitive to irradiation |
| viral infection | cell death by infection with AIDS or influenza virus |
| cancer | death of tumor cells in malignant tissues |
| drug, poison | cell death by antitumor agents or bacterial toxins |
| heat | death of tumor cells by thermotherapy |

As shown in Table 1 above, apoptosis is involved in a great number of vital phenomena. It is suggested that apoptosis is responsible for not only morphogenesis during developmental stages, but also alternation of normal cells (removal of old cells), such as epidermal cells of skin and epithelial cells of small intestine and stomach of mature individuals, atrophy of hormone-dependent tissue thymus by glucocorticoid, atrophy of prostate by castration, elimination of immunocompetent cells which react with self-components, and death of neurons due to the removal of neurotrophic factors.

In addition to such physiological death of cells, apoptosis is also found in the death of cells exposed to irradiation and virus-infected cells. A decrease in T lymphocytes due to AIDS virus has been reported to be also caused by apoptosis, which attracted much attention. Besides these, apoptosis is caused by chemical or physical stimulation, such as administration of medications and poisonous substances, and heat. The death of neurons in neurodegenerative diseases such as Alzheimer's disease, and natural apoptosis of tumor cells and cell death by antitumor agents which occur in malignant tumor lesion have been found to be caused by apoptosis.

Thus, elucidation of molecular mechanisms of apoptosis is crucial for the understanding of biochemical significance and role of cell death in ontogenesis and suppression of carcinogenesis.

The characteristic phenomena commonly observed in apoptosis are morphological changes such as contraction of cell along with the changes in cell membrane (elimination of microbilli) and condensation of chromatin, and fragmentation of chromatin DNA. [Br. J Cancer 26, 239–257 (1972), Nature 284, 555–556 (1980)]. In particular, fragmentation of chromatin DNA into nucleosomal units (FIG. 1) is the most noticeable phenomenon commonly seen in every apoptotic cell, irrespective of the diversity of causative factors of apoptosis, which suggests that apoptosis cascade ends in the process of fragmentation of chromatin DNA.

It has been conventionally suggested that the cleavage of chromatin DNA found in apoptosis is catalyzed by a $Zn^{2+}$ sensitive, endogenous $Ca^{2+}$ dependent endonuclease [J. Immunol. 132, 38–42 (1984), J. Biol. Chem. 266, 18580–18585 (1991), EMBO J. 12, 371–377 (1993), Biochemistry 32, 9129–9136 (1993)].

Motivated by the suggestion, several kinds of endonucleases (Nuc 118, DNase I, DNase II) considered to be the enzymes possibly involved in apoptosis have been recently purified from thymus or cultured cells [Biochem. Biophys. Res. Commun. 39, 254–259 (1970), J. Biol. Chem. 266, 18580–18585 (1991), EMBO J. 12, 371–377 (1993), Arch. Biochem. Biophys. 300, 440–450 (1993)].

However, such enzymes have been purified from normal cells and there is no conclusive proof to show actual involvement of such enzymes in apoptosis.

Therefore, elucidation of endonuclease involved in the fragmentation of chromatin DNA in apoptosis and the control mechanism thereof is extremely important for understanding the whole picture of molecular mechanism of apoptosis, as well as the mechanism of viability and death of cells. It is also useful for developing an agent for the diagnosis, prevention or therapy of cancer, autoimmune diseases, AIDS and the like, in which apoptosis plays certain roles.

DISCLOSURE OF THE INVENTION

The present inventor has studied endonuclease involved in apoptosis, and found three kinds of novel endonucleases in rat thymocyte nuclear fractions, which endonucleases selectively cleaving the linker sites of chromatin DNA to cause DNA fragmentation which characterizes apoptosis. The three kinds of endonucleases were isolated and purified, and further studies of them enabled confirmation that one of them is the endonuclease responsible for the fragmentation of chromatin DNA in apoptosis. The present inventor has succeeded in identifying and obtaining the primary structure of said endonuclease and the nucleotide sequence of the gene thereof, which resulted in the completion of the present invention.

Accordingly, the present invention provides the following:

(1) a novel DNase which is an endonuclease capable of selectively cleaving the linker sites of chromatin DNA, and has the following properties (hereinafter this DNase is referred to as DNase γ):
① Localization: cell nucleus
② Molecular weight: (i) 33,000 (SDS-PAGE (ii) 31,000 (gel filtration)
③ Optimal pH: 7.2
④ Divalent cation dependency: $Ca^{2+}/Mg^{2+}$, $Mn^{2+}$ dependent
⑤ Inhibition by $Zn^{2+}$: $IC_{50}$=40 μM
⑥ DNA cleavage mode: 3'—OH, 5'-P end forming type (2) a novel DNase which is an endonuclease capable of selectively cleaving the linker sites of chromatin DNA, and has the following properties (hereinafter this DNase is referred to as DNase α):
① Localization: cell nucleus
② Molecular weight: (i) 32,000 (SDS-PAGE ) (ii) 28,000 (gel filtration)
③ Optimal pH: 5.6
④ Divalent cation dependency: independent
⑤ Inhibition by $Zn^{2+}$: $IC_{50}$>1 mM
⑥ DNA cleavage mode: 3'-P, 5'-OH end forming type (3) a novel DNase which is an endonuclease capable of selectively cleaving the linker sites of chromatin DNA, and has the following properties (hereinafter this DNase is referred to as DNase β):
① Localization: cell nucleus
② Molecular weight: (i) 32,000 (SDS-PAGE ) (ii) 30,000 (gel filtration)
③ Optimal pH: 5.6
④ Divalent cation dependency: independent
⑤ Inhibition by $Zn^{2+}$: $IC_{50}$>1 mM
⑥ DNA cleavage mode: 3'-P, 5'-OH end forming type (4) the novel DNase of (1) above having the amino acid sequence (amino acid numbers 26–310) substantially shown in Sequence Listing, SEQ ID NO: 1, (5) the novel DNase of (1) above, comprising a precursor polypeptide having an N-terminal precursor peptide region, (6) the novel DNase of (4) above having an amino acid sequence (amino acid numbers 1–25) substantially shown in Sequence Listing, SEQ ID NO: 1 as the N-terminal precursor peptide region, (7) a DNA having a nucleotide sequence encoding the DNase of (1) or any one of (4)–(6) above, preferably a DNA having a nucleotide sequence (nucleotide Nos. 87–941) shown in Sequence Listing, SEQ ID NO: 2, more preferably a DNA having a nucleotide sequence (nucleotide Nos. 1–941) shown in Sequence Listing, SEQ ID NO: 2, (8) a recombinant vector containing the DNA of (7) above,
(9) a host cell transformed with the recombinant vector of (8) above,
(10) a method for producing the DNase described in (1) or any one of (4)–(6) above, comprising culturing the host cell of (9) above and harvesting the DNase from the obtained culture, and
(11) an antibody having an affinity for peptide having the whole or partial amino acid sequence (amino acid numbers 1–310) substantially shown in Sequence Listing, SEQ ID NO: 1.

BRIEF DESCRIPTION OF THE DRAWINGS

FIG. 2A shows DNA extracted from apoptotic rat thymus exposed to irradiation.
FIG. 2B shows DNA extracted from apoptotic rat thymus treated with dexamethasone.

FIG. 5 is a photograph showing an activity gel analysis (electrophoretic images) of DNases α, β and γ:
Lane 1: molecular weight of DNase α purified from normal rat thymus cell nucleus as analyzed by an activity gel system,
Lane 2: molecular weight of DNase β purified from normal rat thymus cell nucleus as analyzed by an activity gel system,
Lane 3: molecular weight of DNase γ purified from apoptosis cell exposed to γ ray radiation as analyzed by an activity gel system,
wherein the molecular weight markers of protein were phosphorylase b (97,400), bovine serum albumin (66,200), ovalbumin (45,000), carbonic anhydrase (31,500), soybean trypsin inhibitor (21,500) and lysozyme (14,400), respectively.

FIG. 6A is a TSKG-2000SW gel filtration HPLC profile of DNase α. FIG. 6B is a TSKG-2000SW gel filtration HPLC profile of DNase β. FIG. 6C is a TSKG-2000SW gel filtration HPLC profile of DNase γ.

FIG. 7A is a photograph showing the pH dependency of DNase α. FIG. 7B is a photograph showing the pH dependency of DNase β. FIG. 7C is a photograph showing the pH dependency of DNase γ.

FIG. 8A shows the activity of purified DNase α (-Δ-), DNase β (-□-) and DNase γ (-574 -) as determined in the presence of 3 mM $CaCl_2$ with increasing concentrations of $MgCl_2$. FIG. 8B is the activity of purified DNase α (-△-), DNase β (-□-) and DNase γ (-●-) as determined in the presence of 3 mM $MgCl_2$ with increasing concentrations of $CaCl_2$; and FIG 8C is the activity determined under optimal conditions of respective DNase with increasing concentrations of $ZnCl_2$.

Lane 1: pretreatment with alkaline phosphatase (APase) and then 3' end labeling
Lane 2: 3' end labeling without pretreatment with APase
Lane 3: 5' end labeling after pretreatment with APase
Lane 4: 5' end labeling without pretreatment with APase FIG. 9A shows fragmented DNA extracted from HeLa S3 cell nuclei digested with DNase α. FIG. 9B shows fragmented DNA extracted from HeLa S3 cell nuclei digested with DNase β. FIG. 9C shows fragmented DNA extracted from HeLa S3 cell nuclei digested with DNase γ.

FIG. 11A shows the fragments liberated by the digestion with Lys-C endopeptidase. FIG, 1B shows the fragments liberated by the digestion, with Asp-N endopeptidase, of the peptide left on PVDF membrane after Lys-C endopeptidase treatment.

DETAILED DESCRIPTION OF THE INVENTION

Figure 1:
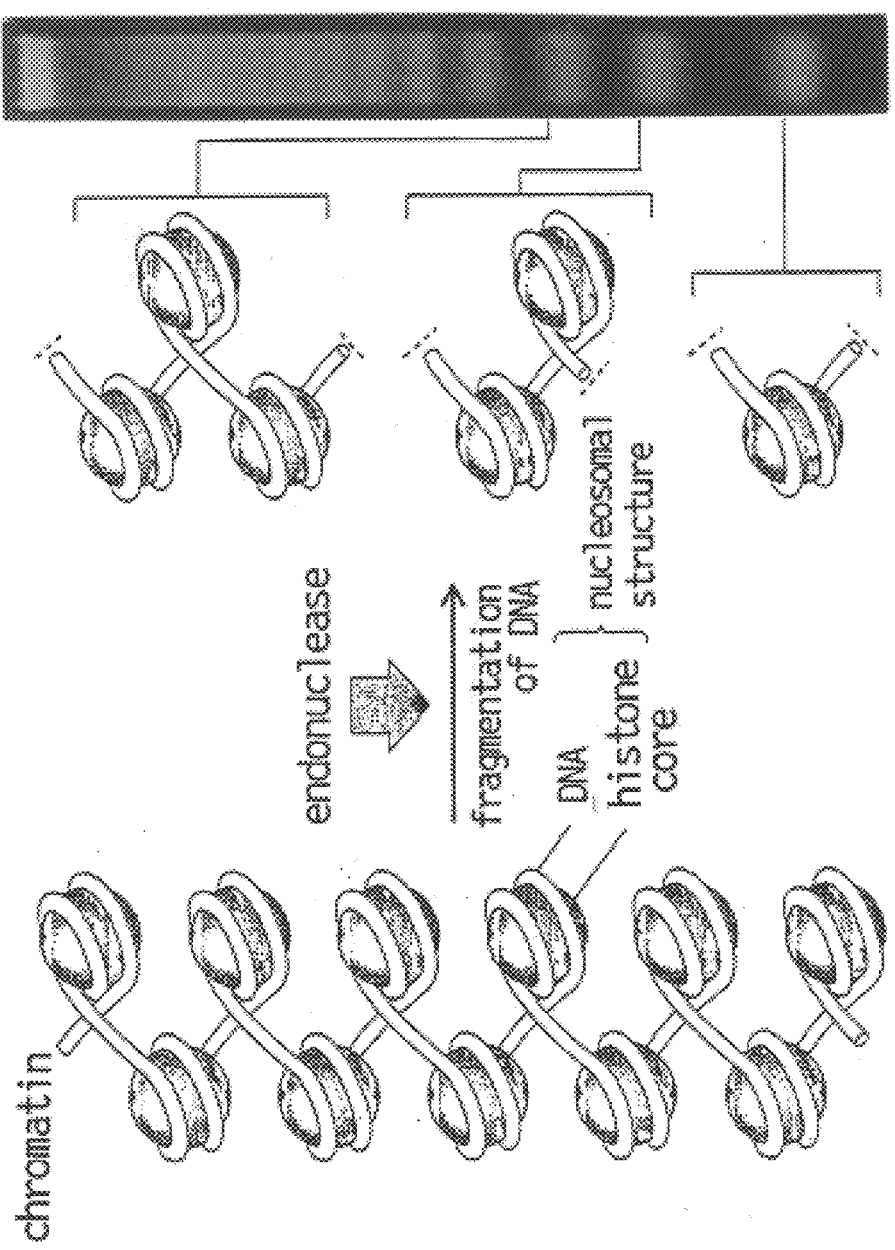
FIG. 1 schematically shows fragmentation of DNA in apoptosis together with a photograph of agarose gel electrophoresis of the fragmented DNA.

The approach for identifying the endonuclease involved in apoptosis is to compare the nature of each fragment of chromatin DNA observed in apoptotic cells and that of DNA fragments fragmented by the endonuclease(s) purified from the nuclei of apoptotic cells.

The fragments of chromatin DNA observed in apoptotic cells show an increasing ratio of small DNA fragments such as nucleosomal monomer and dimer with increasing apoptosis progression time; however, apoptosis does not fragment the entire DNA into monomers but stops at a certain stage. Accordingly, DNA extracted from the apoptotic cells and analyzed by agarose gel electrophoresis shows DNA electrophoretic images of ladder structure having a length integer-fold times longer than the DNA (about 180 bps) contained in nucleosomal monomer.

The fragmentation of DNA which occurs in apoptosis is $Ca^{2+}/Mg^{2+}$ dependent and can be inhibited by $Zn^{2+}$. The produced DNA fragments are 3'-OH/5'-P type double strands having phosphoric acid group at the 5' termini.

(a) DNase γ of the present invention

The DNase γ of the present invention is an endonuclease present in the nuclei of animal cells, preferably the nuclei of the cells derived from thymus, spleen or liver of mammals such as rat and calf, and more preferably in the nuclei of cells derived from calf thymus or rat spleen. Said DNase γ is present, with the same degree of activity, in the nuclei of normal cells and the nuclei of apoptotic cells, irrespective of whether or not apoptosis has been induced. The DNase γ differs from the DNase α and DNase β of the present invention, which lose activity by the induction of apoptosis. As used herein, the apoptosis is not particularly limited by the onset factors and encompasses not only spontaneously generated apoptosis but artificially generated apoptosis as a result of exposure to radiation, glucocorticoid treatment and the like.

The DNase γ of the present invention is a monomeric polypeptide having a molecular weight of about 33,000 by sodium dodecylsulfate-polyacrylamide gel electrophoresis (hereinafter to be referred to as SDS-PAGE), and about 31,000 by gel filtration chromatography. The preferred mode of SDS-PAGE is described in detail in Reference Example 4 quoted in Example 2(1) to be mentioned later, and the preferred mode of gel filtration chromatography is described in detail in Example 2(1) to be mentioned later.

The DNase γ of the present invention is a 3'-OH/5'-P forming type DNase which selectively cleaves the linker sites of chromatin DNA to form mono- or oligonucleosomes having phosphoric acid group at the 5' ends. The optimal pH condition for the activity of said DNase is neutral, preferably pH of about 6.8–about 7.6, more preferably pH of about 7.2, in MOPS-NaOH buffer or Tris-HCl.

The activation of said DNase γ requires the presence of at least both $Ca^{2+}$ and $Mg^{2+}$, or $Mn^{2+}$ alone, which is to be referred to as $Ca^{2+}/Mg^{2+}$ or $Mn^{2+}$ dependent in the present invention. The concentration of said $Ca^{2+}$, $Mg^{2+}$ and $Mn^{2+}$ is 1–3 mM, preferably 3 mM, respectively. More preferably, the both of 3 mM $Ca^{2+}$ and 3 mM $Mg^{2+}$ are present.

The activity of DNase γ is sensitive to $Zn^{2+}$ having micromole concentrations at which $Zn^{2+}$ is known to inhibit apoptosis, and $Zn^{2+}$ having a low concentration of 40 μM inhibits 50% of the activity ($IC_{50}$=40 μM). The activity is completely inhibited by aurintricarboxylic acid, which is an inhibitor of DNase and RNase, at a concentration of 100 μM. However, the activity of said DNase γ is not inhibited by G-actin known to inhibit DNase I.

The DNase γ of the present invention can be produced by a known method such as a method including extraction and purification from the cell nuclei of animal tissues or cells as a starting material, a method by chemical synthesis or genetic recombination. Specific examples include the following method.

The cells derived from thymus, spleen or liver of mammals, such as rat and calf, preferably the cells derived from thymus or spleen of rat or calf as the starting material, are homogenized using a buffer having a pH of neutral range, preferably about 7.8 in the presence of a nonionic detergent to isolate the cell nucleus. Then, the obtained isolated nuclei are subjected to ultrasonic treatment as necessary in the presence of ammonium sulfate (preferable mode being the use of 0.4–0.5 M ammonium sulfate) for solubilization, which is followed by centrifugation to give a supernatant fraction.

The obtained supernatant fraction is applied to column chromatography using, as a carrier, cation exchanger, preferably strong acidic cation exchanger and developed by linear gradient method by salt concentration to obtain an eluted active fraction.

Then, the active fraction is applied to high performance liquid chromatography (hereinafter HPLC) using, as a carrier, cation exchanger, preferably-weak acidic cation exchanger and again developed by linear gradient method by salt concentration. When the fraction is developed with the concentration gradient of KCl using CM5PW column (5 mm I.D.×50 mm, manufactured by Tosoh) as a column, and 20 mM Tris-HCl buffer (pH 7.8) containing 1 mM 2-mercaptoethanol, 0.1 mM PMSF and 10% ethylene glycol as an eluent, the DNase γ of the present invention is eluted at a KCl concentration of about 0.55 M.

Then, the eluted active fraction is subjected to known purification chromatography such as HPLC using heparin column, gel filtration HPLC and HPLC using cation exchanger combined as appropriate to give highly purified monomer DNase γ. The DNase γ thus obtained is subjected to dialysis, centrifugal separation, lyophilization and the like.

The DNase γ of the present invention is considered to be an enzyme involved in DNA fragmentation by apoptosis in thymus or spleen, particularly in rat thymus or spleen, in that the cleavage mode of DNA fragment by said enzyme coincides with that of the DNA fragments produced in rat thymus or spleen cells under apoptosis, they are similar in ion dependency, and said enzyme is present in the rat thymus or spleen cells under apoptosis.

Said DNase γ is useful as one of the tools for elucidating, at a molecular level, apoptosis which occurs in mammals (e.g., cow, horse, mouse, rat, guinea pig and rabbit) inclusive of human, as well as for the development of diagnostic using an antibody of DNase γ, apoptosis-controlling pharmaceutical products containing inhibitor or activating agent of DNase γ; evaluation of apoptosis; and as a basis for establishing apoptotic gene therapy of cancer and autoimmune diseases.

(b) DNase α of the present invention

The DNase α of the present invention is an endonuclease present in the nuclei of animal cells, preferably nuclei of cells derived from thymus, spleen or liver of mammals such as rat and calf, and more preferably an endonuclease present in the nuclei of cells derived from calf thymus or rat spleen. This DNase α exists in the nuclei of normal cells and is scarcely present in the nuclei of apoptotic cells.

The DNase α of the present invention is a monomeric polypeptide having a molecular weight of about 32,000 by SDS-PAGE, and about 28,000 by gel filtration chromatography. The preferred mode of SDS-PAGE is described in detail in Reference Example 4 quoted in Example 2(1) to be mentioned later, and the preferred mode of gel filtration chromatography is described in detail in Example 2(1) to be mentioned later.

The DNase α of the present invention is a 3'-P/5'-OH forming type DNase which selectively cleaves the linker sites of chromatin DNA to form oligonucleosomes having phosphoric acid group at the 3' termini. The optimal pH condition for the activity of said DNase is weak acidic, preferably pH of about 5.4–about 6.0, more preferably pH of about 5.6, in acetate-KOH buffer or MES-NaOH buffer.

The activity of said DNase α is not influenced by the presence or absence of divalent metal ions, such as $Ca^{2+}$, $Mg^{2+}$ and $Mn^{2+}$. It is insensitive to $Zn^{2+}$ and the concentration necessary for inhibiting the activity by about 50% is not less than 1 mM. The activity is completely inhibited by aurintricarboxylic acid, which is an inhibitor of DNase and RNase, at a concentration of 100 PM. However, the activity of this DNase α is not inhibited by G-actin.

The DNase α of the present invention can be produced by a known method such as a method including extraction and purification from animal tissues or cells as a starting material, a method by chemical synthesis or gene recombination. Specific examples include the following method.

That is, the cells from rat thymus are homogenized using a buffer having a neutral pH range, preferably pH of about 7.8, in the presence of a nonionic detergent to isolate the cell nuclei. Then, the obtained isolated nuclei is subjected to ultrasonic treatment as necessary in the presence of ammonium sulfate (preferable mode being the use of 0.15–0.25 M ammonium sulfate) for solubilization, which is followed by centrifugation to give a supernatant fraction.

The obtained supernatant fraction is applied to column chromatography using, as a carrier, cation exchanger, preferably strong acidic cation exchanger, and developed by the linear gradient method by salt concentration to give an eluted active fraction. Then, the active fraction is applied to HPLC using, as a carrier, cation exchanger, preferably weak acidic cation exchanger and again developed by linear gradient method by salt concentration. When the chromatography is developed with the concentration gradient of KCl using CM5PW column (5 mm I.D.×50 mm, manufactured by Tosoh) as a column, and 20 mM Tris-HCl buffer (pH 7.8) containing 1 mM 2-mercaptoethanol, 0.1 mM PMSF and 10% ethylene glycol as an eluent, the DNase α of the present invention is eluted at a KCl concentration of about 0.25 M.

Then, the eluted active fraction is subjected to known purification chromatography such as HPLC using heparin column, gel filtration HPLC and HPLC using cation exchanger combined as appropriate to give a highly purified monomeric DNase α. The DNase α thus obtained is subjected to dialysis, centrifugal separation, lyophilization and the like.

The DNase α of the present invention is useful as a reagent for the analysis of DNA cleavage which occurs in mammals (e.g., cow, horse, mouse, rat, guinea pig and rabbit) inclusive of human and as a basis for the development of an antiviral agent in that this enzyme cleaves viral DNA into a 3'-P/5'-OH forming type.

(c) DNase β of the present invention

The DNase β of the present invention is an endonuclease present in the nuclei of animal cells, preferably the nuclei of cells derived from thymus, spleen or liver of mammals such as rat and calf, and more preferably endonuclease present in the nuclei of cells from calf thymus or rat spleen. This DNase β exists in the nuclei of normal cells and scarcely present in the nuclei of apoptotic cells.

The DNase β of the present invention has a molecular weight of about 32,000 by SDS-PAGE, and about 30,000 by gel filtration chromatography. The preferred mode of SDS-PAGE is described in detail in Reference Example 4 quoted in Example 2(1) to be mentioned later, and the preferred mode of gel filtration chromatography is described in detail in Example 2(1) to be mentioned later.

The DNase β of the present invention is a 31-P/5'-OH forming type DNase which selectively cleaves the linker sites of chromatin DNA to form oligonucleosomes having phosphoric acid group at the 3' termini. The optimal pH condition for the activity of said DNase is weak acidic, preferably pH of about 5.2–about 6.2, more preferably pH of about 5.6, in acetate-KOH buffer or MES-NaOH buffer.

The DNase β has an activity independent of divalent metal cations, such as $Ca^{2+}$, $Mg^{2+}$ and $Mn^{2+}$. It is insensitive to $Zn^{2+}$ and the concentration necessary for inhibiting the activity by about 50% is not less than about 1 mM. The activity is completely inhibited by aurintricarboxylic acid which is an inhibitor of DNase and RNase at a concentration of 100 μM. However, the activity of this DNase β is not inhibited by G-actin.

The DNase β of the present invention can be produced by a known method such as a method including extraction and purification from animal tissues or cells as a starting material, a method by chemical synthesis and genetic recombination. Specific examples include the following method.

That is, the cells from rat thymus, spleen or liver as a starting material are homogenized using a buffer of neutral range, preferably pH of about 7.8, in the presence of a nonionic detergent to isolate the nuclei of the cells. Then, the obtained isolated nuclei are subjected to ultrasonic treatment as necessary in the presence of ammonium sulfate (preferable mode being the use of 0.2–0.3 M ammonium sulfate) for solubilization, which is followed by centrifugation to give a supernatant fraction.

The obtained supernatant fraction is applied to column chromatography using, as a carrier, cation exchanger, preferably strong acidic cation exchanger, and developed by the linear gradient method by salt concentration to obtain an eluted active fraction. Then, the active fraction is applied to HPLC using, as a carrier, cation exchanger, preferably weak acidic cation exchanger and again developed by the linear gradient method by salt concentration. When the fraction is developed with the concentration gradient of KCl using CM5PW column (5 mm I.D.×50 mm, manufactured by Tosoh) as a column, and 20 mM Tris-HCl buffer (pH 7.8) containing 1 mM 2-mercaptoethanol, 0.1 mM PMSF and 10% ethylene glycol as an eluent, the DNase β of the present invention is eluted at a KCl concentration of about 0.35 M.

Then, the eluted active fraction is subjected to known purification chromatography such as HPLC using heparin column, gel filtration HPLC and HPLC using cation exchanger combined as appropriate to give highly purified DNase β. The DNase β thus obtained is subjected to dialysis, centrifugal separation, lyophilization and the like.

The DNase β of the present invention is useful as a reagent for the analysis of DNA cleavage which occurs in mammals (e.g., cow, horse, mouse, rat, guinea pig and rabbit) inclusive of human and as a basis for the development of an antiviral agent in that this enzyme cleaves viral DNA into a 3'-P/5'-OH forming type.

(d) Primary structure (amino acid sequence) of DNase γ of the present invention

The preferable mode of the DNase γ of the present invention is a DNase having an amino acid sequence of the amino acid numbers 26–310 in the amino acid sequence substantially shown in Sequence Listing, SEQ ID NO: 1. Such amino acid sequence is not subject to particular limitation as long as it does not alter the property of said DNase γ, and may include partial substitution, deletion, insertion or modification in the amino acid sequence.

The DNase γ having such amino acid sequence can be produced appropriately using a known method such as a method including extraction and purification from cell nuclei of animal tissues or cells, a method by chemical synthesis and gene recombination. Specific examples include extraction and purification of the cells derived from thymus, spleen or liver of mammals such as rat and calf, and more preferably cells derived from rat spleen, in the same manner as in (a) above. The amino acid sequence of the DNase γ is determined by a direct method by totaling the data obtained by the following ①–④:

① complete hydrolysis of the enzyme to determine the amino acid composition,

② determination of N-terminal by Edman method and the like and that of C-terminal by decomposition with the addition of hydrazine, ③ limited digestion using protease or chemical substance, followed by determination of the amino acid sequence of each fragment by an amino acid sequencer, and ④ the same procedure as in ③ using different protease or chemical substance;

or by an indirect method including cloning of said DNase γ cDNA or genomic DNA and determining the amino acid sequence corresponding to the nucleotide sequence of the coding region (ORF) thereof.

(e) N-Terminal precursor peptide region of DNase γ of the present invention

The DNase γ of the present invention is first synthesized in the cells as a precursor DNase γ having a precursor peptide region at the N-terminal, and then the N-terminal precursor peptide region is cleaved with peptidase to give mature DNase γ.

Said N-terminal precursor peptide region has an amino acid sequence of the amino acid numbers 1–25 in the amino acid sequence substantially shown in Sequence Listing, SEQ ID NO: 1. This amino acid sequence is not subject to particular limitation as long as it does not alter the property of said DNase γ and permits normal processing, and may include partial substitution, deletion, insertion or modification in the amino acid sequence.

The amino acid sequence of the N-terminal precursor peptide region can be determined by cloning cDNA or genomic DNA to determine its nucleotide sequence, and comparing the amino acid sequence corresponding to the nucleotide sequence of ORF included in said nucleotide sequence, and the amino acid sequence near the N-terminal of the mature DNase γ.

(f) DNA encoding the DNase γ of the present invention

While the DNA of the present invention is not subject to particular limitation as long as it is a DNA having a nucleotide sequence encoding the amino acid sequence of the DNase γ of the present invention, it is preferably a DNA encoding the amino acid sequence of the amino acid numbers 26–310 in the amino acid sequence substantially shown in Sequence Listing, SEQ ID NO: 1, more preferably a DNA having a nucleotide sequence of the nucleotide numbers 87–941 in the nucleotide sequence shown in Sequence Listing, SEQ ID NO: 2.

The DNA of the present invention encompasses the DNA encoding the precursor polypeptide of the DNase γ of the present invention having an N-terminal precursor peptide region. To be specific, it is a DNA encoding a DNase γ having, as an N-terminal precursor peptide region, the amino acid sequence of the amino acid numbers 1–25 in the amino acid sequence substantially shown in Sequence Listing, SEQ ID NO: 1., preferably a DNA encoding the amino acid sequence of the amino acid numbers 1–310 in the amino acid sequence substantially shown in Sequence Listing, SEQ ID NO: 1, and more preferably a DNA having a nucleotide sequence shown by the nucleotide numbers 12–941 in the nucleotide sequence shown in Sequence Listing, SEQ ID NO: 2.

In addition, the DNA of the present invention can be obtained by any method. For example, the DNA of the present invention encompasses a complementary DNA (cDNA) prepared from MRNA, a DNA prepared from genomic DNA, a DNA obtained by chemical synthesis, a DNA obtained by amplification by PCR method using RNA (cDNA) or DNA as a template and a DNA constructed by these method in appropriate combination.

For example, a method for cloning the cDNA of DNase γ from a cDNA library derived from the cells producing DNase γ includes the following.

First, MRNA [poly (A) RNA] is prepared from the cells capable of expression and production of DNase γ, such as thymocytes and splenocytes. The MRNA can be prepared by subjecting a whole RNA prepared by a known method such as guanidinethiocyanate method [Chirgwin, J. M. et al., Biochem., 18, 5294 (1979)], heat phenol method and acid guanidine-phenol-chloroform (AGPC) method, to affinity chromatography using oligo(dT)cellulose and poly U-sepharose. Then, using the obtained mRNA as a template, cDNA strand is synthesized by a known method using a reverse transcriptase [Okayama, H. et al., Mol. Cell. Biol., 2, 161 (1982) and ibid, 3, 280 (1983), Gubler, H. and Hoffman, B. J., Gene, 25, 263 (1983)], nick is introduced into the template RNA using RNaseH, and double stranded cDNA is prepared by DNA polymerase I. After end blunting and linker ligation, said cDNA is incorporated into a plasmid vector or phage vector, which is followed by transformation of *Escherichia coli* or in vitro packaging to prepare a cDNA library.

The plasmid vector to be used here is not subject to particular limitation as long as it is replicatable and can be maintained in the host, and the phage vector to be used may be any as long as it can proliferate in the host. Examples of the conventionally used cloning vector include pUC119, λgt10 and λgt11. When it is subjected to screening of antibody to be mentioned later, however, it is preferably a vector having a promoter capable of expressing DNase γ gene in the host.

The method for incorporating cDNA into plasmid includes, for example, the method described in Maniatis, T. et al., Molecular Cloning, A Laboratory Manual, second edition, Cold Spring Harbor Laboratory, 1.53 (1989). The method for incorporating cDNA into phage vector includes, for example, the method described in Hyunh, T. V., DNA Cloning, a practical approach, 1, 49 (1985). For simplicity, for example, a commercially available ligation kit manufactured by Takara Shuzo and the like may be used. The recombinant plasmid and phage vector are inserted into a suitable host, such as prokaryotic cells (e.g., *E. coli* HB 101, DH 5 and MC1061/P3).

The method for incorporating plasmid into host includes, for example, calcium chloride method described in Maniatis, T. et al., Molecular Cloning, A Laboratory Manual, second edition, Cold Spring Harbor Laboratory, 1.74 (1989), calcium chloride/rubidium chloride method and electroporation. The method for incorporating phage vector into the host includes, for example, a method comprising in vitro packaging phage DNA, followed by introducing same into a grown host. The in vitro packaging can be easily performed by the use of commercially available in vitro packaging kit such as that manufactured by Stratagene and Amersham.

The method for isolating the cDNA encoding the DNase γ of the present invention from the cDNA library prepared by the method mentioned above may be a combination of general cDNA screening methods.

For example, an oligonucleotide which is considered to correspond to the partial amino acid sequence of DNase γ is separately synthesized chemically and labeled with $^{32}$P to give a probe, and known colony hybridization [Crunstein, M. and Hogness, D. S.: Proc. Natl. Acid. Sci. USA 72, 3961 (1975)] or plaque hybridization [Molecular Cloning, A Laboratory Manual, second edition, Cold Spring Harbor Laboratory, 2. 108 (1989)] is applied to screen a clone containing the objective cDNA, or a PCR primer is prepared, a certain region of DNase γ is amplified by PCR method, and a clone having a DNA fragment encoding said region is selected. When a cDNA library constructed using a vector capable of expressing cDNA, such as λgt11 phage vector, is used, the objective clone can be selected by the immunoscreening using the antibody against the DNase γ. When a large amount of clone is treated, screening by PCR method is advantageous.

The nucleotide sequence of the thus-obtained DNA can be determined by Maxam-Gilbert method [Maxam, A. M. and Gilbert, W., Proc. Natl. Acad. Sci. USA., 74, 560 (1977)] or dideoxy termination method using phage M13 [Sanger,f. et al., Proc. Natl. Acad. Sci. USA., 74, 5463–5467 (1977)]. The DNase γ cDNA can be obtained by cleaving out part or whole thereof from the clone obtained in the above using a restriction enzyme and the like.

The method for isolating the DNA encoding the DNase γ of the present invention from genomic DNA library is exemplified by the following.

Genomic DNA is prepared from the cells of rat thymus or spleen by a known method such as SDS-phenol method and cetyl trimethylammonium bromide (CTAB) method. RNA is preferably removed by decomposition by ribonuclease. The obtained DNA is partially digested with suitable restriction enzyme and the obtained DNA fragment is amplified with suitable phage or cosmid to prepare a library. The clone having the objective sequence is detected by, for example, a method using a radioactively labeled DNA probe, and part or whole of DNase γ gene is cleaved with restriction enzyme from said clone.

The DNA of the present invention can by chemically synthesized from the nucleotide sequence having the nucleotide numbers 12–941 in the nucleotide sequence depicted in Sequence Listing, SEQ ID NO: 2 by partly or entirely synthesizing the DNA.

(g) The present invention further relates to a recombinant vector containing the above-mentioned DNA encoding DNase γ. The recombinant vector of the present invention is not subject to particular limitation as long as it is capable of maintaining by replication or autoproliferation in various hosts, such as prokaryotic cells and/or eukaryotic cells, and may be plasmid vectors or phage vectors.

These recombinant vectors can be prepared by ligating the DNA encoding the DNase γ of the present invention to commercially available recombinant vectors (plasmid DNA and bacteriophage DNA) by a conventional method. Examples of the usable recombinant vectors include pBR322, pBR325, pUC12, pUC13 as plasmid derived from *Escherichia coli*; pSH19, pSH15 as plasmid derived from yeast; and pUB1IO, pTP5, pC194 as plasmid derived from Bacillus subtilis.

Examples of phage include bacteriophage such as λ phage, and animal and insect viruses such as retrovirus, vacciniavirus and polynuclear virus [pVL1393 (manufactured by Invitrogen)].

For the expression and production of DNase γ, expression vectors are advantageous. The expression vector is not subject to any particular limitation as long as it is capable of expressing DNase γ gene in various host cells such as prokaryotic cells and/or eukaryotic cells, and producing said enzyme.

When bacteria, particularly *Escherichia coli*, is used as a host cell, the expression vector generally consists of at least promoter-operator region, initiation codon, DNA encoding the DNase γ of the present invention, termination codon, terminator region and replicatable unit.

When yeast, animal cell or insect cell is used as a host cell, the expression vector preferably consists of at least promoter, initiation codon, DNA encoding the DNase γ of the present invention and termination codon. In addition, it may contain DNA encoding signal peptide, enhanser sequence, nontranslational region on the 5' side and 3' side of the DNase γ gene of the present invention, splicing junction, polyadenylation site, selection marker region or replicatable unit.

The promoter-operator region for expressing DNase γ of the present invention in bacteria includes promoter, operator and Shine-Dalgarno (SD) sequence (e.g., AAGG). For example, when the host is a bacteria belonging to the genus Escherichia, the region preferably includes Trp promoter, lac promoter, recA promoter, λ PL promoter, lpp promoter, tac promoter and the like. When the host is a bacteria belonging to the genus Bacillus, it is exemplified by SLO1 promoter, SPO2 promoter, penP promoter and the like. Examples of the promoter for expressing DNase γ of the present invention in yeast of eukaryotic cell include PHO5 promoter, PGK promoter, GAP promoter, ADH promoter and the like, and when the host is mammalian cells, it is exemplified by promoter derived from SV40, retrovirus promoter, heat shock promoter and the like, with preference given, but not limited to, SV-40 and retrovirus. The use of enhancer is also effective for expression.

Examples of suitable initiation codon include methionin codon (ATG). Examples of termination codon include conventional termination codon such as TAG, ISA and TAA. The terminator region may be a natural or synthetic terminator conventionally used.

The replicatable unit means DNA capable of replicating the full length DNA sequence in the host cell, and includes, for example, natural plasmid, artificially-modified plasmid (DNA fragment prepared from natural plasmid) and synthetic plasmid. Suitable plasmid is, for example, plasmid pBR322 or artificial modification thereof (DNA fragment obtained by treating pBR322 with a suitable restriction enzyme) for *E. coli*; yeast 2μ plasmid or yeast chromosomal DNA for yeast; and plasmid pRSVneo ATCC 37198, plasmid pSV2dhfr ATCC 37145, plasmid pdBPV-MMTneo ATCC 37224, plasmid pSV2neo ATCC 37149 and the like for mammalian cells.

The enhancer sequence, polyadenylation site and splicing junction site can be those generally used by those skilled in the art, such as those derived from SV40.

The selection marker may be those generally used by a conventional method. Examples thereof include gene resistant to antibiotics, such as tetracycline ampicillin and kanamycin.

The expression vectors of the present invention can be prepared by ligating the above-mentioned promoter, initiation codon, DNA encoding DNase γ of the present invention, termination codon and terminator region successively and cyclically into a suitable replicatable unit. When desired, a suitable DNA fragment (e.g., linker and other restriction site) can be used by a conventional method such as digestion with restriction enzyme and ligation using T4DNA ligase.

(h) The transformed cells of the present invention can be prepared by introducing the above-mentioned expression vector into a host cell.

The host cell of the present invention is not subject to any particular limitation as long as it is capable of adapting to the aforesaid expression vector and can be transformed, and is exemplified by various cells such as natural cells and artificially prepared recombinant cells conventionally used in the technical field of the present invention [e.g., bacteria (bacteria belonging to the genus Escherichia and bacteria belonging to the genus Bacillus), yeast (genus Saccharomyces and genus Pichia), animal cell and insect cell].

Preferred are *Escherichia coli* and animal cells which are exemplified by *Escherichia coli* (DH5, HB101), mouse-derived cells (COP, L, C127, Sp2/0, NS-1 and NIH3T3), rat-derived cells, hamster-derived cells (BHK and CHO), monkey-derived cells (COS1, COS3, COS7, CV1 and Velo) and human-derived cells (Hela, cell derived from diploid fibroblast, myeloma cells and Namalwa).

The expression vector can be introduced into host cell (transformation or transfection) by a method known per se. For example, the method of Cohen et al. [Proc. Natl. Acad. Sci. USA., 69, 2110 (1972)], protoplast method [Mol. Gen. Genet., 168, 111 (1979)] or competent method [J. Mol. Biol., 56, 209 (1971)] can be used for bacteria (*Escherichia coli*, *Bacillus subtilis*); the method of Hinnen et al. [Proc. Natl. Acad. Sci. USA., 75, 1927 (1978)] or lithium method [J. Bacteriol., 153, 163 (1983)] can be used for *Saccharomyces cerevisiae*; the method of Graham [Virology, 52, 456 (1973)] can be used for animal cell; and the method of Summers et al. [Mol. Cell. Biol.3, 2156–2165 (1983)] can be used for insect cell for transformation.

(i) The DNase γ of the present invention can be produced by culturing the transformed cells (hereinafter used in the sense embracing transfectants) containing the expression vector prepared as mentioned above, in a nutrient medium.

The nutrient medium preferably contains carbon source, inorganic nitrogen source or organic nitrogen source necessary for the growth of host cell (transformant). Examples of carbon source include glucose, dextran, soluble starch and sucrose; examples of inorganic or organic nitrogen source include ammonium salts, nitrates, amino acids, corn steep liquor, peptone, casein, meat extract, soybean lees, potato extract solution and the like. Where desired, other nutrient sources such as inorganic salts (e.g., calcium chloride, sodium dihydrogenphosphate and magnesium chloride), vitamins, and antibiotics (e.g., tetracyclin, neomycin, ampicillin, kanamycin and the like) may be added.

Culture is performed by a method known in the pertinent field. The culture conditions, such as temperature, pH of medium and culture time are appropriately selected to allow mass production of DNase γ.

Specific examples of medium and culture conditions to be determined according to the host cell are shown by way of non-limiting examples in the following.

When the host is bacteria, actinomyces, yeast, or filamentous fungus, a liquid medium containing the above-mentioned nutrient sources is preferable, with preference given to a medium having pH of 5–8.

When the host is *E. coli*, preferable medium includes, for example, LB medium and M9 medium [Miller. J., Exp. Mol. Genet, p.431, Cold Spring Harbor Laboratory, New York (1972)]. In this case, culture is performed at 14–43° C. for about 3–24 hours with aeration and agitation as necessary.

When the host is bacteria belonging to the genus Bacillus, culture is performed at 30–40° C. for about 16–96 hours with aeration and agitation as necessary.

When the host is yeast, examples of the medium include Burkholder minimum medium [Bostian. K. L. et al, Proc. Natl. Acad. Sci. USA, 77, 4505 (1980)], and pH is preferably 5–8. Culture is performed at 20–35° C. for about 14–144 hours with aeration and agitation as necessary.

When the host is animal cell, examples of the medium include MEM medium containing about 5–20% fetal calf serum [Science, 122, 501 (1952), DMEM medium [Virology, 8, 396 (1959)], RPMI1640 medium [J. Am. Med. Assoc., 199, 519 (1967)], 199 medium [Proc. Soc. Exp. Biol. Med., 73, 1 (1950)], and the like. The pH of medium is about 6–8, and culture is performed at 30–40° C. for about 15–72 hours with aeration and agitation as necessary.

When the host is insect cell, examples of the medium include Grace's medium containing fetal calf serum (Proc. Natl. Acad. Sci. USA, 82, 8404 (1985)], and pH is preferably about 5–8. Culture is performed at 20–400C for about 15–100 hours with aeration and agitation as necessary.

The DNase γ of the present invention can be obtained by the following method from the culture obtained by the above-mentioned incubation.

That is, when the DNase γ of the present invention is present in the culture liquid in the culture, the culture filtrate (supernatant) a is obtained by filtration or centrifugal separation of the culture, which is followed by purification and isolation of DNase γ according to a conventional method generally used for purification and isolation of the natural or synthetic protein from such culture filtrate.

Ad Examples of the method for purification and isolation include a method utilizing the solubility, such as salting out and solvent precipitation; a method utilizing difference in molecular weights such as dialysis, ultrafiltration, gel filtration and sodium dodecylsulfate-polyacrylamide gel electrophoresis; a method utilizing charges, such as ion exchange chromatography and hydroxylapatite chromatography; a method utilizing specific affinity such as affinity chromatography; a method utilizing difference in hydrophobicity such as reversed-phase high performance liquid chromatography; and a method utilizing difference in isoelectric point such as isoelectric focusing.

When the DNase γ of the present invention is present in periplasm or cytoplasm of the cultured transformant, the culture is treated by a conventional method such as filtration and centrifugal separation to collect microbial cells or cells, which are suspended in suitable buffer, subjected to ultrasonic treatment, treatment with lysozyme, freeze-thaw and the like to destroy the cell wall and/or cell membrane of the cells and subjected to centrifugal separation, filtration and the like to give membrane fraction containing DNase γ. Said membrane fraction is solubilized with a surfactant such as Triton-X100 to give a crude solution. This crude solution is treated by a conventional method exemplified supra for isolation or purification. When the DNase γ is present in the nuclei of the cultured transformant cells, the cell wall and cell membrane are destroyed by a conventional method to isolate the nuclei, which was followed by ultrasonic treatment and the like to destroy the nucleus membrane, centrifugation treatment to give supernatant, and treatment of the supernatant by a conventional method mentioned above for isolation and purification.

(j) The present invention also relates to an antibody having affinity for the above-mentioned DNase γ, a precursor polypeptide thereof or a peptide containing part of the amino acid sequence thereof. The antibody of the present invention encompasses both polyclonal antibody and monoclonal antibody having the above properties. Said monoclonal antibody embraces monoclonal antibodies belonging to an immunoglobulin class such as IgG, IgM, IgA, IgD and IgE, with preference given to IgG or IgM immunoglobulin class monoclonal antibody.

The antibody of the present invention can be obtained by a conventional method (Zoku-Seikagaku Jikken Koza 5, Men-eki Seikagaku Kenkyuho, ed. the Japanese Biochemical Society: published by Tokyo Kagaku Dojin, and others). For example, the polyclonal antibody of the present invention can be prepared by the following method. That is, a mixture of a complex of a (poly)peptide having partial or full length amino acid sequence of DNase γ of the present invention which is crosslinked with a carrier protein such as bovine serum albumin and Keyhole Limpets Hemocyanin (KLH), and complete (incomplete) Freund's adjuvant [FCA (FIA)] is used as an antigen to immunize mammals such as rabbit, mouse, rat, guinea pig and hamster. The mammal is given one to four boosters every 1–4 weeks from the initial immunization, partial blood is taken at about 3–10 days after each booster, and the antibody titer of the serum of the blood sample is measured utilizing the antigen-antibody reaction to confirm increase thereof. The whole blood is taken about 3–10 days after the final immunization and antiserum is purified.

The monoclonal antibody against the DNase γ of the present invention can be produced from hybridoma (fused cell) produced by so-called cell fusion. That is, a fused hybridoma is formed from antibody-producing cells and myeloma cells, and the hybridoma is cloned. Using, as an antigen, a (poly)peptide having partial or full length amino acid sequence of DNase γ or precursor thereof of the present invention, a clone which produces an antibody having specific affinity therefor is selected. The steps therefor are known per se except the use, as immunogen, of (poly) peptide having partial or full length amino acid sequence of DNase γ or precursor thereof of the present invention.

The immunogen can be prepared by admixing (poly) peptide having partial or full length amino acid sequence of DNase γ or precursor thereof of the present invention with complete (incomplete) Freund's adjuvant. The animal to be the target of immunization is exemplified by mammals such as mouse, rat, guinea pig, hamster and rabbit, with preference given to mouse and rat, and more preference given to mouse. The immunization is performed by subcutaneous, intramuscular, intravenous, intra-footpad or intraperitoneal injection to the mammals once to several times. In general, booster is given once to four times about every one to four weeks from the initial immunization, and the final immunization is performed about one to four weeks thereafter. About 3–10 days after the final immunization, antibody-producing cells are collected from the immunized animals.

The hybridoma which secretes monoclonal antibody can be prepared by the method of Kohler and Milstein et al (Nature, Vol. 256, pp. 495–497, 1975) or a modified method analogous thereto. That is, the monoclonal antibody of the present invention is prepared by culturing hybridoma obtained by the fusion of the antibody-producing cell contained in spleen, lymph node, bone marrow or tonsil, preferably spleen, obtained from the animal immunized as mentioned above, and myeloma of the same species of mammals such as mouse, rat, guinea pig, hamster, rabbit and human, more preferably mouse, rat or human. The culture may be performed in vitro or in vivo such as in mammals (e.g., mouse, rat, guinea pig, hamster and rabbit), preferably mouse and rat, more preferably ascites of mouse, and the antibody can be obtained from respective culture supernatant, or ascites of mammals. The myeloma cells to be used for cell fusion includes, for example, mouse-derived myeloma P3/X63-AG8, P3/NSI/1-Ag4-1, P3/X63-Ag8.U1, SP2/O-Ag14, FO and BW5147; rat-derived myeloma 210RCY3-Ag1.2.3.; and human-derived myeloma U-266AR1, GM1500-6TG-A1-2, UC729-6, CEM-AGR, DIR11 and CEM-T15. The fused cell clone which produces monoclonal antibody of the present invention can be screened by, for example, culturing the fused cells in a microtiter plate, and determining the reactivity of the culture supernatant in the well suggesting growth by an enzyme antibody method such as RIA and ELISA.

The monoclonal antibody can be isolated and purified by subjecting the sera or ascites containing the monoclonal antibody of the present invention obtained by the method mentioned above to ion exchange chromatography (DEAE or DE52), or affinity column chromatography using anti-immunoglobulin column or protein A column.

The production of the monoclonal antibody of the present invention is not limited to the above-mentioned production methods but may be obtained by any method. In general, the monoclonal antibody has structurally different sugar chains depending on the kind of the mammals to be immunized. The monoclonal antibody of the present invention is not limited by the structural difference of the sugar chain, but encompasses monoclonal antibodies derived from any mammal. Moreover, monoclonal antibody of the present invention encompasses human monoclonal antibody obtained using transgenic mouse created by genetic engineering by incorporating human immunoglobulin gene, so that it can produce human antibody; chimeric monoclonal antibody produced by recombining certain mammal-derived monoclonal antibody constant region (Fc region) for human monoclonal antibody Fc region by genetic recombination; and chimeric monoclonal antibody wherein the entire region except CDR (complementarity determining region) capable of directly binding to antigen complementarily has been recombined for the corresponding region of human monoclonal antibody.

EXAMPLE

The present invention is explained more clearly in the following by way of Examples and Reference Examples, to which the invention is not limited.

Reference Example 1
Induction of apoptosis

The thymus was removed from 10 weeks old male rat (albino Wister rat) and suspended in Krebs-Ringer phosphate solution containing 10 mM glucose. The thymus was exposed to 10 Gy $^{60}$Co γ-ray irradiation or treated with $10^{-7}$ M dexamethasone, which was followed by incubation at 37° C. for 4 hours to induce apoptosis. The treated apoptotic thymus was morphologically observed in an electron microscope and analyzed for DNA fragment by 2% agarose gel electrophoresis.

Reference Example 2
Characteristics of apoptosis in rat thymus

The apoptosis in rat thymocytes which was induced by γ-ray irradiation or treatment with dexamethasone according to Reference Example 1 was characterized by morphological changes of apoptotic cells and the property of DNA fragment.

(1) Morphological changes of apoptotic cells

The rat thymus exposed to γ-ray irradiation was observed in a transmission electron microscopy. A comparison with normal thymus clearly revealed morphological changes such as condensation of chromatin in the nucleus and disappearance of microvilli on the cell surface, which are characteristically seen in apoptosis. The similar morphological changes were observed in the rat thymus treated with dexamethasone.

(2) Properties of DNA fragment produced in apoptotic cells
(i) Behavior of DNA fragment on agarose gel electrophoresis The apoptotic cells induced by γ-ray irradiation were dissolved in lysis buffer (50 mM Tris-HCl (pH 7.8), 10 mM EDTA, 0.5% w/v N-lauronyl sarcosylate NaI. The obtained DNA was thoroughly treated with 0.5 mg/ml RNase A for 20 minutes and 0.5 mg/ml proteinase K for 30 minutes, after which it was subjected to 2% agarose gel electrophoresis. The pattern of the DNA fragment stained with ethidium bromide was observed in photograph taken under UV illumination [Biochem. Biophys. Res. Commun., 194, (1993), ppl 30–31].

As a result, 2% agarose gel electrophoresis of nuclear DNA fraction of the cells derived from irradiated thymus showed a ladder pattern which is characteristic of apoptosis, suggesting cleavage between nucleosomes of chromatin DNA. The agarose gel electrophoresis of the DNA of the cells derived from dexamethasone-treated thymus also showed the similar behavior.

(ii) DNA cleavage mode

The DNA cleavage mode in apoptotic thymocytes induced by irradiation or treatment with dexamethasone was studied by the end labeling method to be mentioned later. If the produced nucleosomal DNA fragments are of the type having phosphoric acid group at the 5' termini, and free 3' termini (3'-OH/5'-P forming type), this DNA could be labeled at the 3' termini by treating with terminal deoxynucleotidyl transferase (hereinafter referred to as TdT) and α-$^{32}$P-deoxycytidine triphosphate [hereinafter referred to as (α-$^{32}$P) dCTP], without pretreatment with alkaline phosphatase, and only when treated with alkaline phosphatase, 5' termini can be labeled by the treatment with polynucleotide kinase and T-3$^{2}$P-adenosine triphosphate [hereinafter referred to as (γ-$^{32}$P)ATP].

End labeling method

DNA was isolated from apoptotic rat thymus obtained in Reference Example 1 by phenol/chloroform extraction.

The 3' terminal of the obtained DNA was labeled by incubation of DNA fragments with TdT (5U; manufactured by Takara Shuzo) and [α-$^{32}$P]dCTP (0.83 mCi/ml; manufactured by Du Pont) in the presence of 25 mM Tris-HCl (pH 7.6), 10 mM DTT and 1 mM CaCl$_2$.

The 5' terminal was labeled by incubation of DNA fragments with T4 polynucleotide kinase (5U; manufactured by Takara Shuzo) and (γ-$^{32}$P)ATP (0.83 mCi/ml; manufactured by Du Pont) in the presence of 100 mM Tris-HCl (pH 7.6), 20 mM MgCl$_2$, 10 mM DTT and 0.2 mM spermidine.

When the terminal of DNA strand has a phosphoric acid group, it is removed by the pretreatment with calf small intestine alkaline phosphatase (20U; manufactured by Takara Shuzo) in the presence of 36 mM Tris-HCl (pH 8.0) and 1 mM MgCl$_2$.

After labeling, the labeled DNA was recovered from nucleotide which was not used for the labeling by treating with ammonium acetate/isopropanol to allow precipitation. The labeled DNA was subjected to 2% agarose gel electrophoresis and the DNA in the gel was transferred onto a nylon membrane which was then subjected to autoradiography.

Figure 2:
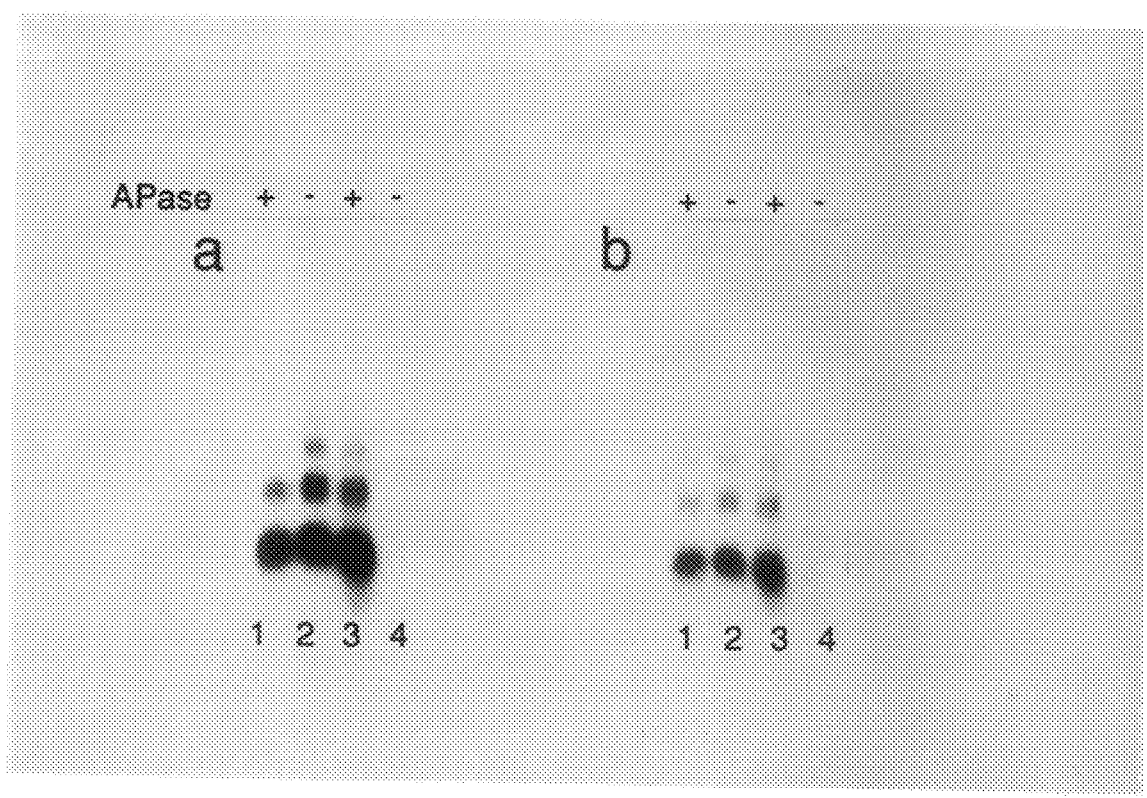
FIG. 2A and FIG. 2B are photographs showing the autoradiograph, after 2% agarose gel electrophoresis, of a part of DNA which was extracted from rat thymus under apoptosis and analyzed by end labeling method:
Lane 1: DNA incubated with alkaline phosphatase (APase) before labeling 3' end
Lane 2: DNA incubated in the absence of APase before labeling 3' end
Lane 3: DNA incubated in the presence of APase before labeling 5' end
Lane 4: DNA incubated in the absence of APase before labeling 5' end

The obtained autoradiograms are shown in FIG. 2A and FIG. 2B. FIG. 2A a is DNA derived from thymus under apoptosis induced by irradiation, and FIG. 2B is DNA derived from thymus with apoptosis induced by treatment with dexamethasone. As is evident from the figures, production of DNA fragment having 3'-OH and 5'-P termini were evidenced in the apoptotic thymus induced by the exposure to irradiation or the treatment with dexamethasone. The results reveal that apoptosis was catalyzed by endonuclease which produced 3'-OH/5'-P cleavage termini of DNA strand.

Reference Example 3
Assay of endonuclease (DNase) activity
(1) Assay 1

The activity of endonuclease (DNase) can be assayed by observing fragmentation of chromosomal DNA in the nucleus on 2% agarose gel electrophoresis using, as a substrate, the nucleus of HeLa S3 cell (human cervical carcinoma epithelial cell) which is completely free of endogenous endonuclease [Biochem. Biophys. Res. Commun. 194, (1993), pp, 30–31].

To be specific, a reaction mixture (30 μl) of HeLa S3 cells (1.67×10$^7$/ml) and DNase fraction is incubated at 37° C. for 60 minutes and the reaction is stopped by cooling same on ice. Then, the reaction mixture after reaction is centrifuged at 20,000× g for 20 seconds, and the precipitated nuclei are dissolved in a lysis buffer [50 mM Tris-HCl (pH 7.8), 10 mM EDTA, 0.5% w/v N-lauronyl sarcosylate Na]. The obtained DNA is thoroughly treated with 0.5 mg/ml RNase A for 20 minutes and with 0.5 mg/ml proteinase K for 30 minutes, after which they are subjected to 2% agarose gel electrophoresis. The pattern of the DNA fragments stained with ethidium bromide were observed in photograph taken under UV illumination. The ratio of fragmentation (percent fragmentation) is calculated from the density of DNA fragments with a molecular weight of less than 5 kb.

(2) Assay 2

The activity of endonuclease (DNase) can be assayed by observing fragmentation of chromosomal DNA on 0.8% agarose gel electrophoresis using, as a substrate, supercoiled pBSIISK(-) plasmid.

To be specific, a reaction mixture (30 μl) of supercoiled pBSIISK(-) plasmid (6.67 mg/ml) and DNase fraction is treated at 37° C. for 10 minutes and the reaction is stopped by cooling same on ice. Then, the reaction mixture after reaction is treated with phenol/chloroform to extract plasmid DNA. The aqueous layer is subjected to 0.8% agarose gel electrophoresis. The pattern of the DNA fragment stained with ethidium bromide is observed in photograph taken under UV illumination. The ratio of fragmentation (percent fragmentation) is calculated from the density of DNA fragments with a molecular weight of less than 5 kb.

As a suitable reaction solution for the assay of the activity of DNases α and β, 50 mM MES-NaOH (-pH 5.6) buffer containing 3 mM $MgCl_2$, 1 mM 2-mercaptoethanol and 0.1 mM PMSF is used. As a suitable reaction solution for the assay of the activity of DNase γ, 50 mM MOPS-NaOH (pH 7.2) buffer containing 3 mM $CaCl_2$, 3 mM $MgCl_2$, 1 mM 2-mercaptoethanol and 0.1 mM PMSF is used.

Reference Example 4

DNase-activity gel system

The DNase-activity gel system by Rosenthal et al. [Anal. Biochem. 80, 76–90 (1977)] was used after some modification, so as to identify the active product of DNase and to determine the molecular weight thereof.

That is, various DNases purified and obtained in Example 1 were separated by electrophoresis in Laemmli SDS-PAGE gel containing native calf thymus DNA (200 μg/ml). The calibration of the molecular weight using standard proteins on SDS gel was not influenced by the presence of double stranded DNA (200 μg/ml) in SDS gel.

After electrophoresis, the gel was washed with 10 mM Tris-HCl (pH 7.8) and 5 mM 2-mercaptoethanol at 50° C. for one hour to remove SDS, and stood in 10 mM Tris-HCl (pH 7.8) overnight at 40C to allow refolding of said DNase. The gel was incubated for appropriate time at 37° C. using a solution containing 10 mM Tris-HCl (pH 7.8), 3 mM $CaCl_2$ and 3 mM $MgCl_2$.

After staining the gel with ethidium bromide and transillumination of UV, obvious nuclease activity was detected on the fluorescent background as a dark region.

Example 1

Purification of DNases α, β and γ

Unless specifically indicated, the following treatments were conducted at 0–4° C.

The rat thymus was homogenized in buffer A [10 mM Tris-HCl (pH 7.8), 2 mM 2-mercaptoethanol, 0.3 mM PMSF, 3 MM $MgCl_2$] containing 0.1% Noidet P-40 (NP-40). The homogenate was centrifuged at 600× g for 10 minutes. The sedimented nuclear fractions containing mitochondria were collected, and supernatant was centrifuged at 150,000× g for one hour. The sediment fraction was referred to as membrane fraction containing microsome and the supernatant was referred to as cytosol fraction.

The endonuclease activity present in each of the obtained fraction was assayed according to the method described in Reference Example 3. As a result, the activity of about 65%, 25% and 10% was found in the nucleus fraction containing mitochondria, membrane fraction containing microsome, and the cytosol fraction, respectively. Then, using the nucleus fraction as a starting material, endonuclease was purified.

The DNase active product in the nuclear fraction was solubilized by ultrasonic treatment in buffer A containing 0.5M ammonium sulfate, and the debris of the nuclei was removed by centrifugation at 150,000× g for one hour.

The obtained supernatant (extract from nuclei) was subjected to S Sepharose column (1 cm I.D.×13 cm; manufactured by Pharmacia) equilibrated with buffer N [20 mM Tris-HCl (pH 7.8), 1 mM 2-mercaptoethanol, 0.1 mM PMSF, 10% ethylene glycol]. The column was washed with buffer N, and developed by linearly increasing the salt concentration (KCl) of the buffer N from 0 M to 1 M (300 minutes, flow rate 0.15 ml/min). As a result of the assay according to Assay 1 of Reference Example 3, the DNase active product was recovered as a single peak eluted at 0.6 M KCl. This active product was subjected to HPLC using a CM5PW column (5 mm I.D.×50 mm; manufactured by Tosoh) equilibrated with buffer N. and eluted with a linear gradient of 0–1 M KCl (35 min) of buffer N (flow rate 0.3 ml/min).

Figure 3:
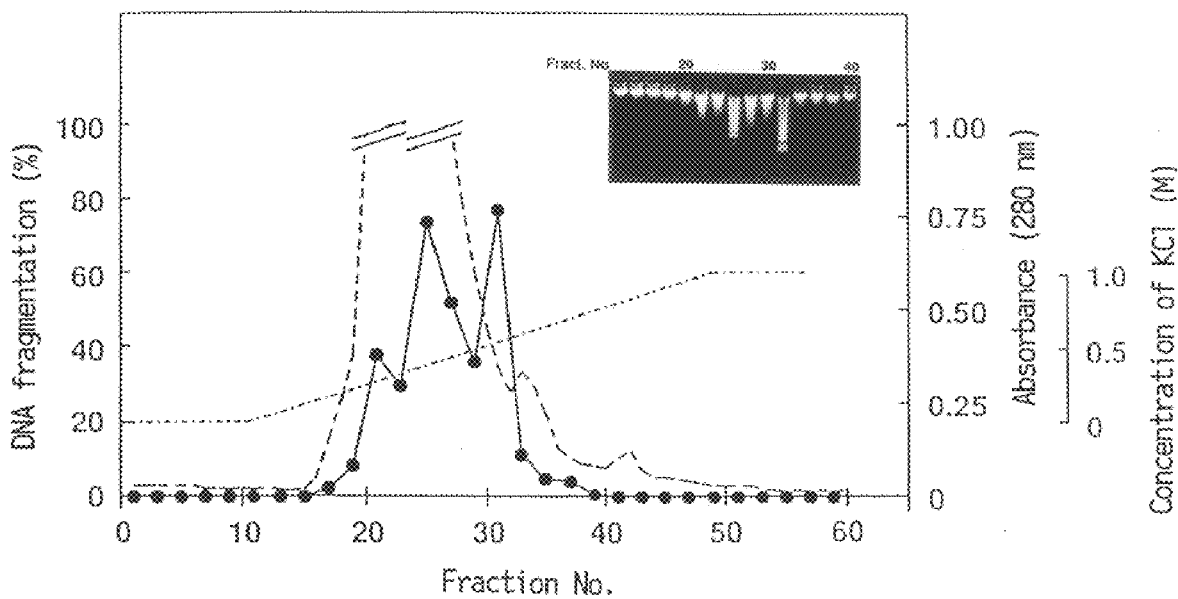
FIG. 3 shows the HPLC (CM5PW column) profile of DNase active fractions derived from normal rat thymus, which were obtained using S Sepharose, and agarose gel electrophoretic image of each fraction.

As a result, the activity of endonuclease was found in three fractions eluted at the concentration of about 0.24 M, 0.34 M and 0.55 M KCl, respectively, which were named DNases α, β and γ according to the order of elution (FIG. 3).

The respective active fractions (DNase α, DNase β and DNase γ) were purified by successive HPLC using heparin 5PW, G2000SW and CM5PW columns.

Specifically, each DNase fraction was applied to heparin 5PW column (5 mm I.D.×50 mm; manufactured by Tosoh) equilibrated with buffer N, and the protein was developed and eluted with buffer N with the linear gradient of 0–1 M KCl (35 min, flow rate:0.3 ml/min). The eluted active fraction was then purified by gel filtration HPLC (flow rate:0.5 ml/min) using G2000SW column (8 mm I.D.×30 cm; manufactured by Toso) equilibrated with buffer S [20 mM MOPS-NaOH (pH 7.0), 1 mM 2-mercaptoethanol, 0.1 mM PMSF, 5% ethylene glycol] containing 0.3 M NaCl. The obtained DNase fraction was ultimately subjected to HPLC using CM5PW column (5 mm I.D.×50 mm; manufactured by Tosoh) equilibrated with buffer S containing 0.3 M NaCl and the objective DNase was developed and eluted with buffer S with the linear gradient of 0.3–1.5 M NaCl (35 min, flow rate:0.3 ml/min).

The obtained DNase fraction was dialyzed against buffer S and preserved at 0–4° C.

The DNase activity in each fraction obtained by HPLC was determined by the method described in Reference Example 3 (1).

As a result of these chromatographys, it was found that every DNase did not show formation of complex or structural interconversion. That is, DNases α, β and γ are considered to be present as monomeric polypeptide.

Figure 4:
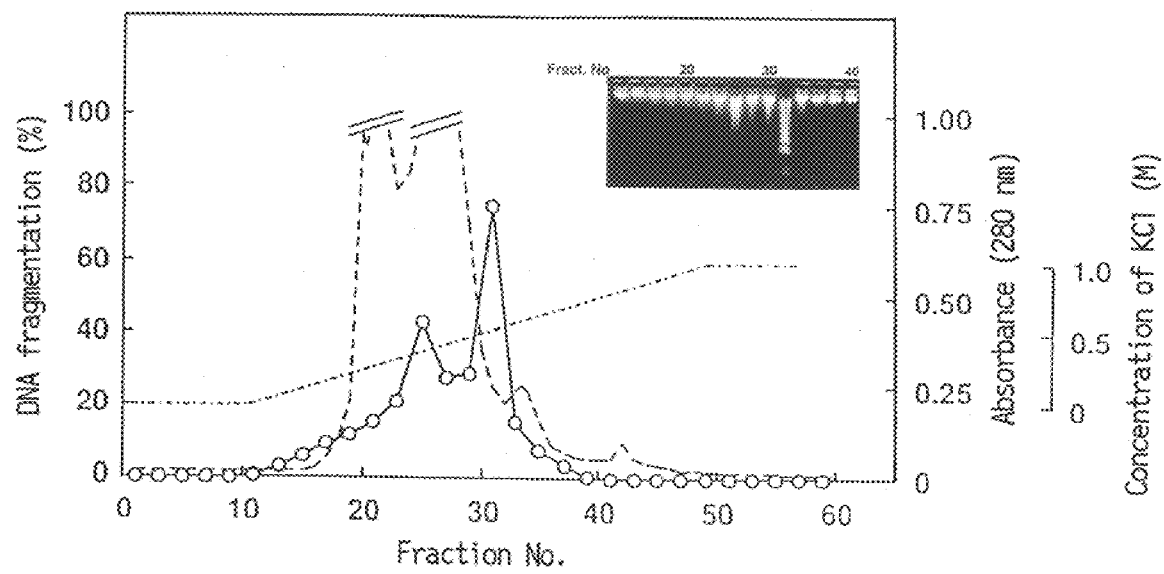
FIG. 4 shows the HPLC (CM5PW column) profile of DNase active fractions derived from rat thymus under apoptosis, which were obtained using S Sepharose, and agarose gel electrophoretic image of each fraction.

The CM5PW HPLC profile for purification of the nuclei of the cells derived from apoptotic thymus exposed to irradiation is shown in FIG. 4. It was found therefrom that the activity of DNases α and β decreases when apoptosis was induced by irradiation, whereas DNase γ activity was not influenced at all. The similar results were found in the apoptotic thymus treated with dexamethasone.

Example 2 properties of DNase (1) Molecular weight

The molecular weight of DNases α, β and γ purified according to Example 1 was determined by SDS-PAGE regeneration (activity gel system) described in Reference Example 4. This activity gel system is based on the ability of DNase which is regenerated after removal of SDS and decomposes DNA during incubation.

The localization of DNase in the gel can be detected as a dark band of the ethidium bromide-fluorescent background due to the disappearance of DNA fluorescence. The results are shown in FIG. 5. Addition of $Ca^{2+}/Mg^{2+}$ to the solvent for incubation with DNase γ resulted in a non-fluorescent band at the site corresponding to 33 kDa protein (lane 3). DNase α (lane 1) and DNase β (lane 2) both showed non-fluorescent bands at the sites corresponding to 32 kDa protein.

Figure 6:
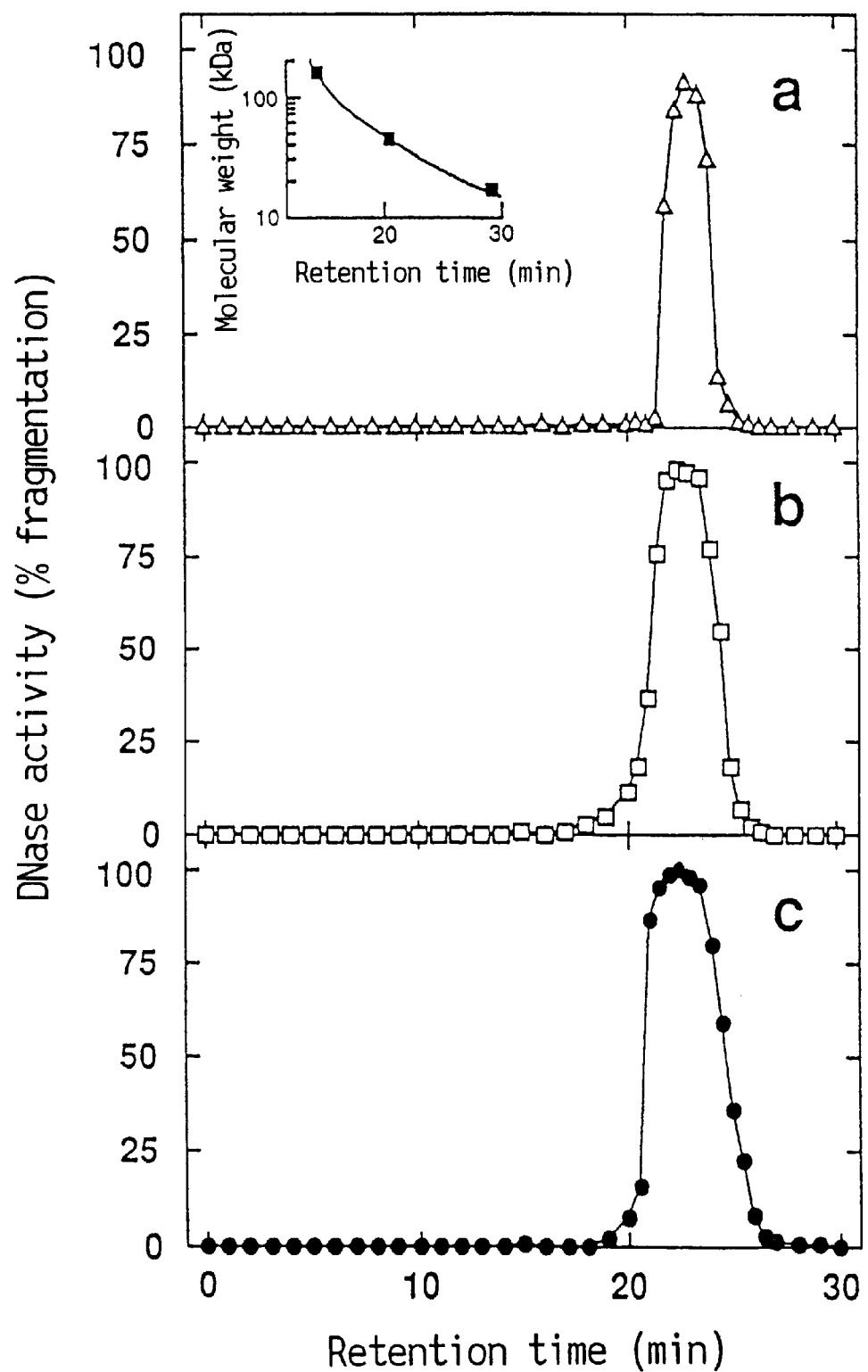
FIG. 6A, FIG. 6B, and FIG. 6C show TSKG-2000SW gel filtration HPLC profile of DNase α, DNase β and DNase γ, in which elution was done at flow rate 0.5 ml/min. Note that the insertion into FIG. a shows a calibration of molecular weight standard product [IgG (158,000), ovalbumin (44,000) and myoglobin (17,000)].

The DNases α, β and γ were respectively subjected to gel filtration HPLC (flow rate:0.5 ml/min, eluate: buffer S [20 mM MOPS-NaOH (7.0), 1 mM 2-mercaptoethanol, 0.1 mM PMSF, 5% ethylene glycol] containing 0.3 M NaCl using G2000SW column (8 mm I.D.×30 cm; manufactured by Tosoh), as a result of which they were detected as a single peak at 28 kDa (FIG. 6A), 30 kDa (FIG. 6B) and 31 kDa (FIG. 6C).

(2) Optimal pH of DNase

The optimal pH for the activity of DNases α, β and γ was determined by assaying HeLa S3 nuclei in various buffers from acidic to basic (Reference Example 3, Assay 1) and calculating from the percentage of DNA fragmentation.

Figure 7:
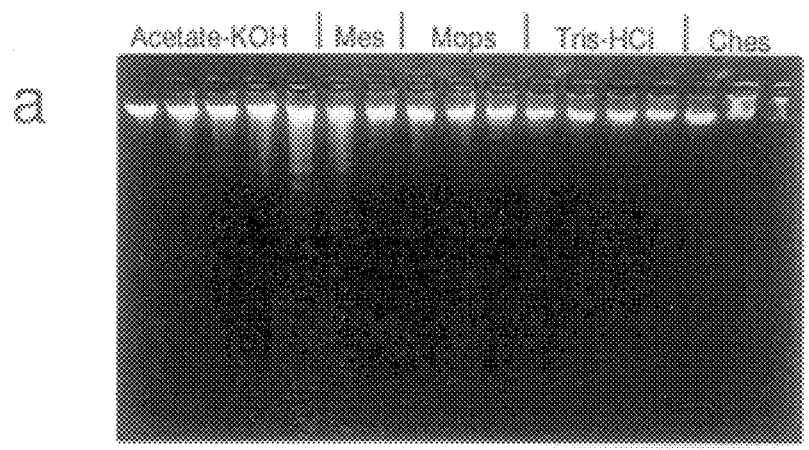
FIG. 7A, FIG. 7B, and FIG. 7C are photographs (agarose gel electrophoretic images) showing the pH dependency of DNase α, DNase β and DNase γ. The activity of purified DNases α, β and γ was respectively determined in acidic to basic (from left to right facing the photograph) buffers. The results are shown from the left end lane in the photograph in acetic acid-KOH buffer (pH 4.0, pH 4.4, pH 4.8, pH 5.2 and pH 5.6), MES-NaOH buffer (pH 5.6 and pH 6.2), MOPS-NaOH buffer (pH 6.8, pH 7.2 and pH 7.6), Tris-HCl buffer (pH7.4, pH 7.8, pH 8.2 and pH 9.0) and CHES-NaOH buffer (pH 8.6, pH 9.4 and pH 10.4).
Figure 7:
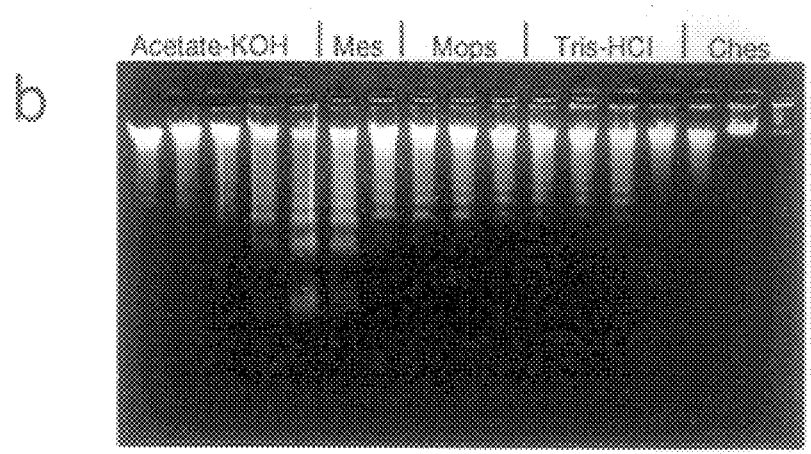
Figure 7:
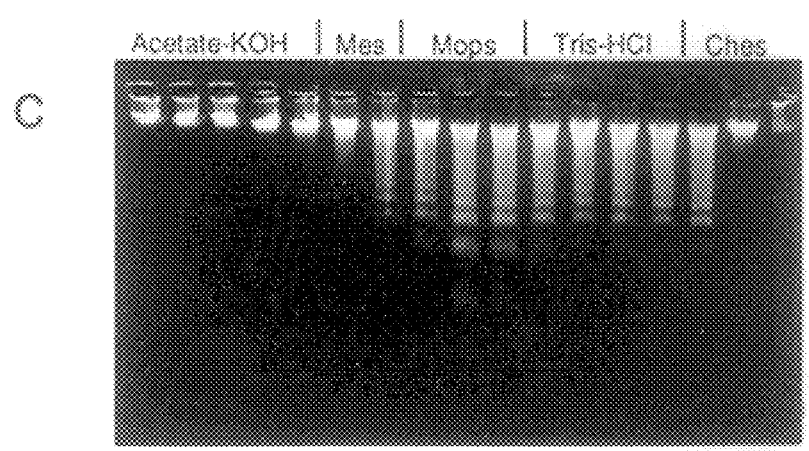

The results [pH dependency of DNases α (FIG. 7A), β (FIG. 7B) and γ (FIG. 7C) in HeLa S3 nuclear assay system] The buffers used for the assay were, from the left end lanes of FIG. 7A, FIG. 7B, and FIG. 7C, acetic acid-KOH buffer (pH 4.0, pH 4.4, pH 4.8, pH 5.2 and pH 5.6), MES-NaOH buffer (pH 5.6 and pH 6.2), MOPS-NaOH buffer (pH 6.8, pH 7.2 and pH 7.6), Tris-HCl buffer (pH 7.4, pH 7.8, pH 8.2 and pH 9.0) and CHES-NaOH buffer (pH 8.6, pH 9.4 and pH 10.4). As is evident from the results, the activity of DNase α was seen in acetic acid-KOH buffer (pH 5.6)—MES-NaOH buffer (pH 5.6), the activity of DBase β was seen in acetic acid-KOH buffer (pH 5.6)—MES-NaOH buffer (pH 5.6 and 6.2), and the optimal pH was about 5.6 for both. On the other hand, the activity of DNase γ was maximum at near pH 7.2 of MOPS-NaOH buffer and the optimal pH was considered to be about 7.2.

(3) Effects of divalent cations

Figure 8:
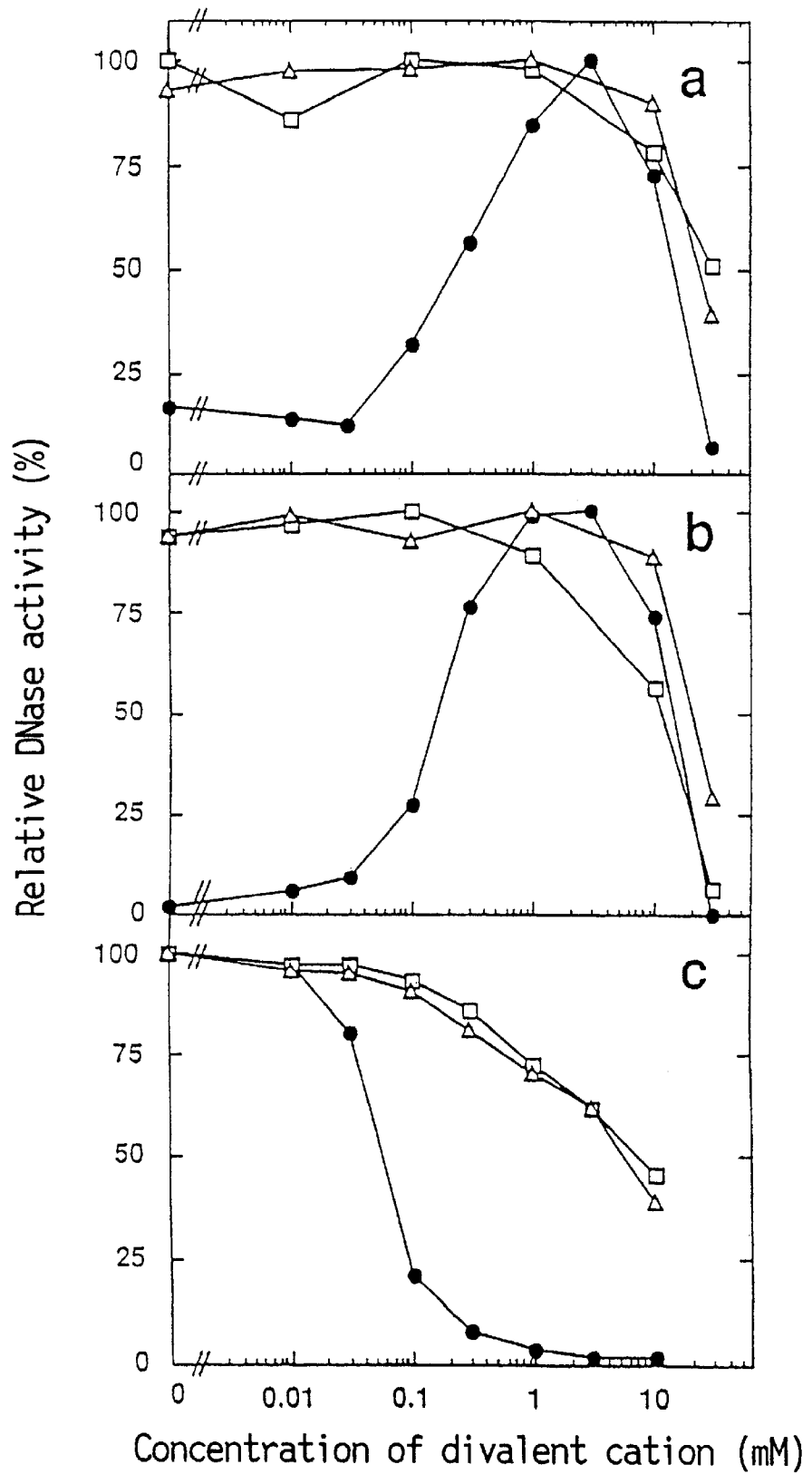
FIG. 8A, FIG. 8B, and FIG 8C show the effects of divalent cations on the activity of DNases α, β and γ.

Effects of divalent cations on the activity of DNase α, DNase γ and DNase γ were examined. To be specific, the effect of $Mg^{2+}$ was examined by assaying the activity of purified DNases α, β and γ in the presence of 3 mM $CaCl_2$ with increasing concentrations of $MgCl_2$. The effect of $Ca^{2+}$ was examined by assaying the activity of DNases α, β and γ purified in the same manner, with increasing concentrations of $CaCl_2$ in the presence of 3 mM $MgCl_2$. The effect of $Zn^{2+}$ was examined in 50 mM HES-NaOH (pH 5.6) buffer containing 3 mM $MgCl_2$, 1 mM 2-mercaptoethanol and 0.1 mM PMSF with increasing concentrations of $ZnCl_2$ with regard to DNases α and β, and it was examined in 50 mM MOPS-NaOH (pH 7.2) buffer containing 3 mM $CaCl_2$, 3 mM $MgCl_2$, 1 mM 2-mercaptoethanol and 0.1 mM PMSF, with increasing concentrations of $ZnCl_2$ with regard to DNase γ. The results are shown in FIG. 8, FIG. 8B, and FIG. 8C. As a result, DNase γ required both $Ca^{2+}$ and $Mg^{2+}$ for full activity, wherein the optimal concentration of the both was 1–3 mM (FIG. 8A and FIG. 8B). DNase γ was sensitive to $Zn^{2+}$, and its activity was inhibited by 50% by $Zn^{2+}$ with a low concentration of 40 $\mu$M (FIG. 8c).

On the other hand, the activity of DNase α and DNase β was not influenced by $Mg^{2+}$ or $Ca^{2+}$, and was not influenced by $Zn^{2+}$ up to the concentration of 1 mM. However, the presence of metallic ion with high concentrations of 10–30 mM inhibited DNase activity of DNases α and β, like DNase γ.

The endonuclease activity of each DNase under the conditions shown in Table 2 is shown [according to Reference Example 2 (1) Assay 1].

The activity of DNases α and β was calculated relative to the endonuclease activity which was assayed using HeLa S3 cell nuclear chromatin DNA as a substrate and 50 mM MES-NaOH (pH 5.6) buffer containing 3 mM $MgCl_2$, 1 mM 2-mercaptoethanol and 0.1 mM PMSF as a reaction solution, and taken as 100%; and the activity of DNase γ was calculated relative to the endonuclease activity which was assayed using HeLa S3 cell nuclear chromatin DNA as a substrate and 50 mM MOPS-NaOH (pH 7.2) buffer containing 3 mM $CaCl_2$, 3 mM $MgCl_2$, 1 mM 2-mercaptoethanol and 0.1 mM PMSF as a reaction solution, and taken as 100%. In the Table, "−" means deletion of said components from the above-mentioned optimal reaction mixture and "+" means addition of said components to the above-mentioned optimal reaction mixture.

TABLE 2

| | DNase activity (%) | | |
|---|---|---|---|
| condition | α | β | γ |
| optimal condition | 100 | 100 | 100 |
| ⎡ $Mg^{2+}/Ca^{2+}$ (mM) | 3/0 | 3/0 | 3/3 |
| ⎣ optimal pH | 5.6 | 5.6 | 7.2 |
| | (MES—NaOH) | (MES—NaOH) | (MOPS—NaOH) |
| $-Mg^{2+}$ | 92 | 94 | 16 |
| $-Ca^{2+}$ | | | 1 |
| −2-mercaptoethanol | 115 | 119 | 96 |
| −PMSF | 81 | 102 | 94 |
| $+Mg^{2+}$ (3 mM) | 104 | 102 | |
| $+Ca^{2+}$ (3 mM) | 101 | 104 | |
| $+Mn^{2+}$ (3 mM)($-Mg^{2+}/Ca^{2+}$) | 104 | 103 | 45 |
| $+Zn^{2+}$ (0.1 mM) | 90 | 93 | 21 |
| +G actin (100 μg/ml) | 99 | 97 | 98 |
| +aurintricarboxylate | | | |
| (30 μM) | 32 | 0 | 29 |
| (100 μM) | 0 | 0 | 0 |

(4) Hydrolysis mode of DNase γ

Figure 9:
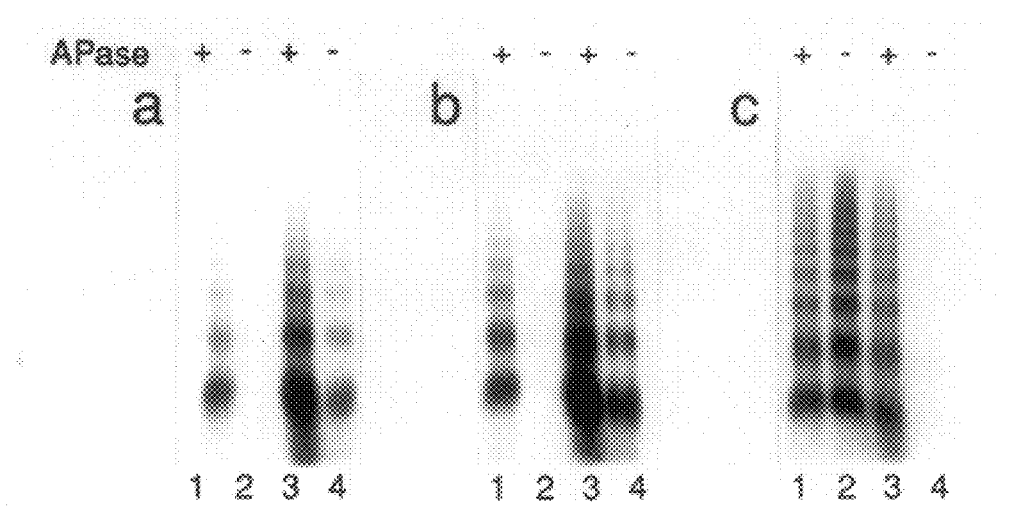
FIG. 9A, FIG. 9B, and FIG. 9C includes photographs showing fragmentation of DNA by DNases α, β and γ (on autoradiograph after 2% agarose gel electrophoresis)

The characteristic of DNase γ as shown in (1)–(3) above suggests that DNase γ is possibly the endonuclease involved in DNA fragmentation in apoptosis. Then, whether or not the DNA treated with DNase γ produces fragment having 3'-OH/5'-P termini was investigated according to the end labeling method described in Reference Example 2 (2) (ii). The results are shown in FIG. 9A, FIG. 9B, and FIG. 9C. As is evident from the results, the same labeling pattern was seen as that seen in Reference Example 2 (FIG. 2A and FIG. 2B) when the purified DNA derived from HeLa S3 cell nuclei digested with DNase γ (FIG. 9C in the figure) was end-labeled. During the end-labeling, the 5' termini of the DNA fragments were not labeled unless pretreated with alkaline phosphatase (FIG. 9A, FIG. 9B, and FIG. 9C, lane 4). Therefrom it was clarified that DNase γ produced 3'-OH/5'-P termini of DNA strands.

On the other hand, the 3' termini of the DNA fragments produced by DNases α (FIG. 9A) and β (FIG. 9B) were labeled with TdT only after the pretreatment with alkaline phosphatase, and the 5' termini all reacted without pretreatment with alkaline phosphatase, which clarified that they had 3'-P/5'-OH termini.

From the above experiment results, the following can be said about the properties and physiological significance of DNases α, β and γ.

That is, these three kinds of DNase are present as monomeric polypeptides in the cell nuclei, and cleave the linker regions of chromatin DNA to produce nucleosomal oligomers. The DNases α and β were both obtained from the nuclei by easy solubilization, from which it is considered that they are endonucleases present in the nucleoplasm. On the other hand, DNase γ could not be solubilized without ultrasonic treatment under high salt concentrations, which suggested that it was strongly bound to a certain nuclear structure.

The DNase γ of the present invention is an endonuclease present in cell nuclei, which requires both $Ca^{2+}$ and $Mg^{2+}$ for its activity. The termini of the DNA fragments cleaved with this DNase γ are of the same type as the termini of the DNA fragments produced by apoptotic rat thymus and are of 3'-OH/5'-P forming type. The activity of DNase γ is also inhibited by $Zn^{2+}$ of $\mu M$ order known to inhibit apoptosis. Therefrom it is considered that DNase γ is the endonuclease which participates in the DNA fragmentation of thymic apoptosis.

The DNases α and β of the present invention are different from the above-mentioned DNase γ in physical and enzymatic properties, and the difference was noticeable in the cleavage mode of chromosomal DNA and divalent metal cation dependency.

The presence of an enzyme having the same form as DNases α and β in the cell nuclei of calf thymus and cell nuclei of rat spleen and liver suggests the important role of DNases α and β in the DNA metabolism and digestion of viral DNA among the nuclear functions.

Example 3
cDNA cloning of DNase γ
(1) Mass purification of DNase γ

The rat thymocytes had low DNase γ activity (protein amount), and an enough amount of protein for determining partial amino acid sequence was not available. Thus, DNase γ was purified from splenocytes having high DNase γ activity.

Unless otherwise indicated, the following treatments were performed at 4° C.

The rat splenocytes (100 g) were homogenized in buffer A [10 mM Tris-HCl (pH 7.8), 2 mM 2-mercaptoethanol, 0.3 mM PMSF, 3 mM $MgCl_2$] containing 0.3% Noidet P-40 (NP-40). The homogenate was centrifuged at 600× g for 10 minutes. The sedimented nuclear fractions were collected, and DNase active substance in the nuclear fractions was solubilized by ultrasonic treatment in buffer A containing 0.3 M ammonium sulfate. The debris of the nuclei was removed by centrifugation at 150,000× g for one hour.

The obtained supernatant (extract from nuclei) was applied to S-cartridge (manufactured by Bio-Rad) equilibrated with buffer N [20 mM Tris-HCl (pH 7.8), 1 mM 2-mercaptoethanol, 0.1 mM PMSF, 2.5% ethylene glycol]. The column was washed with buffer N, and developed by linearly increasing the salt concentration (KCl) in the buffer N from 0 M to 1 M (50 minutes, flow rate:2.0 ml/min). As a result of the assay according to Assay 1 of Reference Example 3, the DNase active substance was recovered as a single peak eluted at 0.6 M KCl. The active substance fractions were subjected to HPLC using a CM5PW column (5 mm I.D.×50 mm; manufactured by Tosoh) equilibrated with buffer N, and eluted with a linear gradient of 0–1 M KCl (30 min) of buffer N (flow rate:0.3 ml/min).

The DNase γ active fractions eluted at 0.55 M KCl were purified by successive HPLC using heparin 5PW, TSKG2000SW and SP5PW columns.

Figure 10:
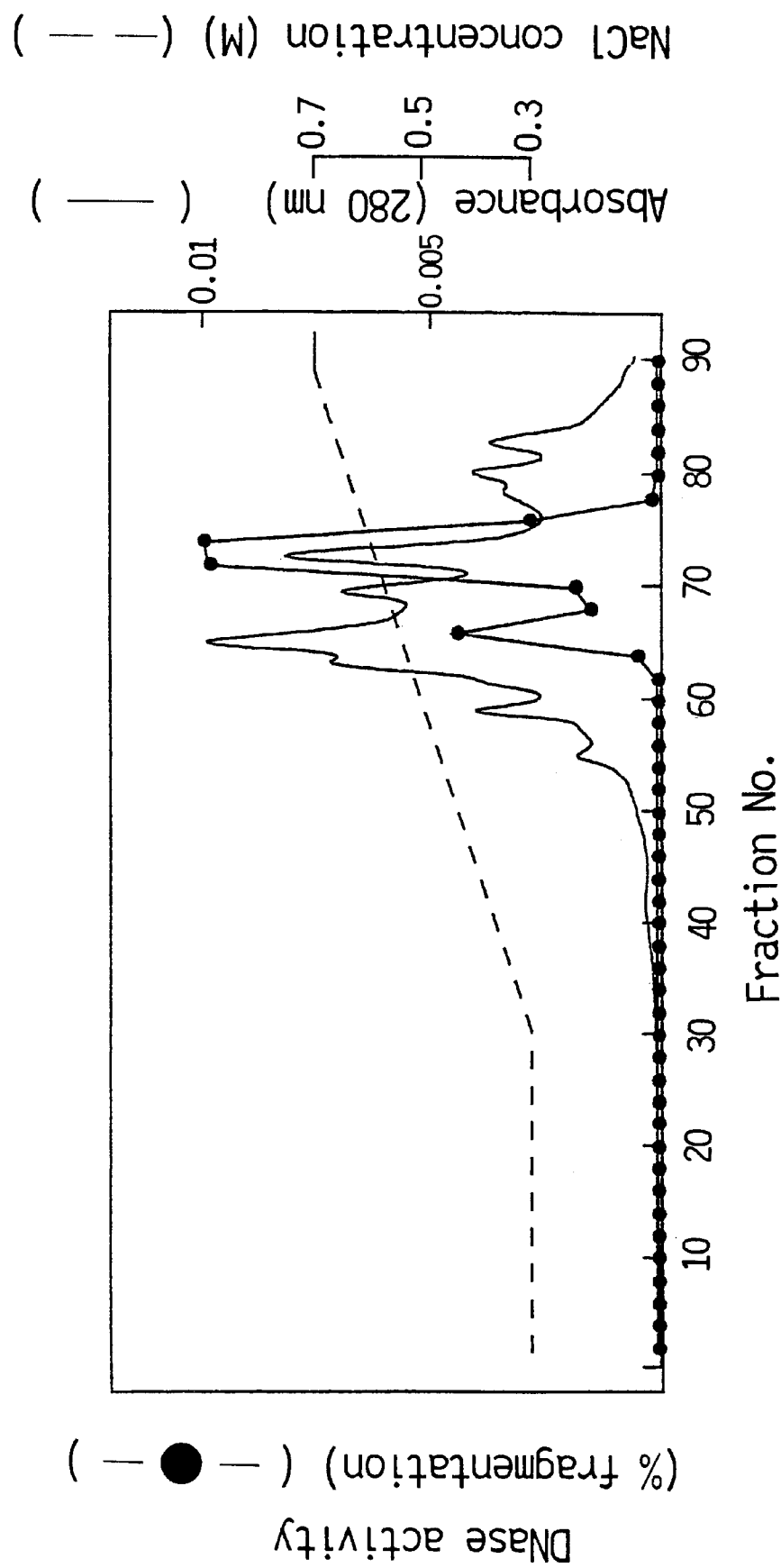
FIG. 10 shows SP5PW HPLC profile, wherein DNase activity of each fraction is shown by -●-, absorbance of each fraction at 280 nm is shown by ——and NaCl concentration gradient is shown by - -.

Specifically, each DNase fraction was applied to heparin 5PW column (5 mm I.D.×50 mm; manufactured by Tosoh) equilibrated with buffer N. and the protein was developed and eluted with buffer N with the linear gradient of 0–1 M KCl (30 min, flow rate:0.3 ml/min). The eluted active fractions were purified by gel filtration HPLC (flow rate:0.5 ml/min) using TSKG2000SW column (8 mm I.D.×30 cm; manufactured by Tosoh) equilibrated with buffer M [20 mM MES-NaOH (pH 5.6), 1 mM 2-mercaptoethanol, 0.1 mM PMSF, 2.5% ethylene glycol] containing 0.3 M NaCl. The obtained DNase γ fractions were ultimately subjected to HPLC using SP5PW column (5 mm I.D.×50 mm; manufactured by Tosoh) equilibrated with buffer M, and developed and eluted with buffer S with the linear gradient of 0.3–0.7 M NaCl (35 min, flow rate:0.3 ml/min). The profile of SP5PW HPLC is shown in FIG. 10. The DNase γ active fractions eluted at 0.58 M NaCl were collected and subjected to SDS-PAGE. The DNase activity (FIG. 10) was determined by the method of Reference Example 3 (1).

(2) Determination of partial amino acid sequence of DNase γ

The purified DNase γ fractions obtained by SP5PW HPLC were precipitated by trichloroacetic acid, and subjected to 10% acrylamide SDS-PAGE by a conventional method [Laemmli, U. K., Nature, 227: 680–685 (1970)] to detect 33 kDa band (FIG. 10) by silver staining. Then, the band of DNase γ protein was transferred onto a PVDF membrane (manufactured by Millipore) by electroblotting using a mini-trans blot cell (manufactured by Bio-Rad). Using part thereof, the N terminal amino acid sequence (Table 3) was determined by gas phase protein sequencer (PSQ-1, manufactured by Shimazu Corporation).

Figure 11:
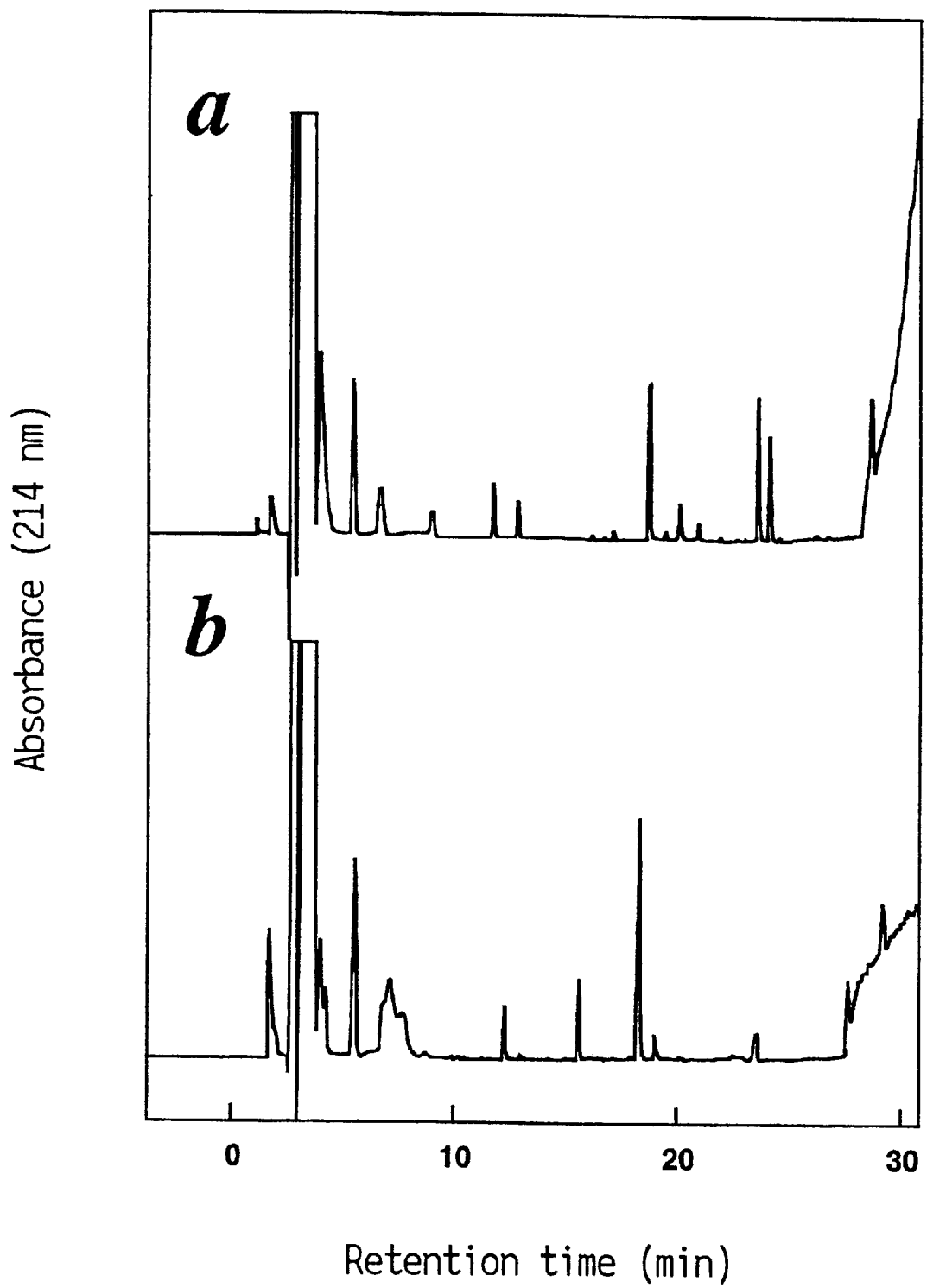
FIG. 11A and FIG. 11B show separation, by reversed phase HPLC, of DNase γ fragments limitatively digested by endopeptidase.

With regard to the rest, an excess mercaptoethanol was added to reduce the disulfide bond in the protein to sulfhydryl, and said sulfhydryl was alkylated with iodoacetic acid to give an S-carboxymethyl derivative. The PVDF membrane bound with the DNase γ protein was placed in a buffer containing a Lys-C endopeptidase (enzyme which specifically cleaves the peptide bond on the carboxyl side of the lysine residue of peptide) and reacted at 37° C. After the enzyme digestion, each peptide fragment liberated from the membrane was separated and collected by reversed-phase HPLC. The fraction containing peptide was monitored at wavelength 214 nm (FIG. 11a).

Each fraction of the fragment which was detected as a peak was dried by a centrifugal evaporator, dissolved in SDS solution and subjected to gas phase protein sequencer (PSQ-1, manufactured by Shimazu Corporation) for amino acid analysis to determine partial amino acid sequence of each peptide fragment [Table 3 wherein (K) means lysine residue cleaved by enzymatic digestion].

The peptide still bound on the membrane was treated by the method mentioned above with Asp-N endopeptidase (enzyme specifically cleaves the peptide bond on the amino side of the aspartic acid residue of the peptide) and the obtained peptide fragments were separated and recovered by reversed-phase HPLC (FIG. 11b) in the same manner to determine amino acid sequence (Table 3).

TABLE 3 amino acid sequences of rat DNase γ digestion fragments

| treatment | amino acid sequence |
| --- | --- |
| N-terminal | LRLTSFNXR |
| Lys—C end peptidase digestion | (K)ENHNAMDIIV |
| | (K)EQYAFLYK |
| | (K)DFVIVPLHTTPE |
| | (K) AENFIFMG |
| Asp—N end peptidase digestion | DVFS |

X: unidentified amino acid (3) cDNA Library

As the rat spleen cDNA library, a commercially available rat spleen 5'-STRETCH cDNA Library (manufactured by Clonetech) was used. This library comprised cDNA (average size: 1.8 kb) clone ($2 \times 10^6$ independent clone) which was prepared from mRNA extracted and purified from whole spleen of adult rat (male, Sprague-Dawley) using oligo(dT) random primer, and inserted into the EcoRI site of λgt 11 vector via adaptor.

(4) Preparation of DNA probe

Based on the nucleotide sequences assumed from the underlined sequences from among the partial amino acid sequences of DNase γ as shown in Table 3, oligo DNA probes were synthesized. The nucleotide sequences of said oligo DNA probes are shown in Table 4. When the codon corresponding to the last amino acid could not be focused to a single one, synthesis was not done.

TABLE 4 nucleotide sequences of oligo DNA probes

| amino acid sequence | nucleotide sequence | number of nucleotide |
| --- | --- | --- |
| KENHNA | 5'-AARGARAAYCAYAAYGC-3' | 17 mer |
| KEQYAFL | 5'-AARGARCARTAYGCNTTYYT-3' | 20 mer |
| KDFVIV | 5'-AARGAYTTYGTNATHGT-3' | 17 mer |
| DVFS | 5'-GARGTNTTYTC-3' | 11 mer |

R: A or G, Y: T or C, N: A, G, T or C, H: T, C or A (5) Screening

① Preparation of filter for screening

*Escherichia coli* Y1090r- was incubated in an LB medium (40 ml) containing 0.2% maltose and 10 mM $MgSO_4$ overnight and the bacterial cells were recovered by centrifugation. Then, the cells were suspended in 30–40 ml of 10 mM $MgSO_4$. The suspension (200 µl) and λgt 11 phage solution of (3) above containing rat cDNA were mixed, and SM 10 buffer [10 mM Tris-HCl (pH 7.6), 10 mM $MgCl_2$, 68 mM NaCl, 0.1 mg/ml gelatin] was added to make the total amount 400 µl, which was followed by incubation at 37° C. for 20–30 minutes.

The mixture of *Escherichia coli* and phage was plated on a 1.5% LB agar medium containing 10 mM $MgSO_4$, and LB top agarose (6 ml, 60–65° C.) was added and thoroughly mixed. When the top agarose became solid, it was incubated at 37° C. overnight.

After incubation, said plate was stood still at 4° C. for one hour. Then, a nylon filter (manufactured by Pall Corporation) was placed on the top agarose to effect transfer. The nylon filter was treated in a denaturing solution for 20 seconds, and then in a neutralizing solution for 20 seconds. The filter was dried on a filter paper and immobilized by UV illumination.

② Labeling of probe

The oligo DNA probe prepared in (4) above was labeled at the 5' terminal with $^{32}P$ using [γ-$^{32}P$]ATP and T4 kinase. A reaction solution having the following composition was incubated at 37° C. for 30 minutes.

10 ng/µl oligo DNA 1 µl
10× kinase buffer 4 µl
[γ-$^{32}P$]ATP 10 µl
UPW 23 µl
T4 kinase 2 µl ③ Plaque hybridization A prehybridization solution was prepared as in the following.

5× Denhardt solution
6× SSPE solution
0.25% SDS
40 µg/ml heat-denatured salmon sperm DNA The filter prepared in the above ① was placed in said prehybridization solution and left standing at 37° C. overnight. Then, the labeled probe prepared in the above ② was mixed with a suitable amount of prehybridization solution and hybridized at 37° C. for 18 hours using 5 µl of probe solution per filter.

After hybridization, the filter was washed with 2× SSC containing 0.1% SDS, and the filter was placed in 2× SSC containing 0.1% SDS, which was followed by washing with shaking at 42° C. for 1–1.5 hours. This step was repeated three times. The filter was dried on a filter paper and subjected to autoradiography (3 days).

According to the autoradiography, the top agarose corresponding to the signal indicating a positive clone was taken out and placed in 500 µl of 1× λ buffer, which was left standing at room temperature for 30–60 minutes. A $10^3$-fold dilution (1–10 µl) was mixed with a suspension (200 µl) of *Escherichia coli* Y1090r-. Using said mixture, the steps of the above ①–③ were repeated to run a secondary screening, whereby single plaques were separated. As a result, 16 positive clones were obtained. Said positive clones were again infected with *Escherichia coli* Y1090r-, and plated in such a manner as to allow growth of the plaque in the entirety of one plate of an LB agar medium plate, and the λ gt 11 phage DNA was recovered. The details of the phage DNA recovery method followed the method of Maniatis et al. [Molecular Cloning, A Laboratory Manual, second edition 2.64 (1989)].

(6) Confirmation of cDNA insert by Southern method

The recovered phage DNA was treated with BsiwI to cleave out a cDNA insert. A part thereof was subjected to agarose gel electrophoresis, and the length of the insert was confirmed by ethidium bromide staining. After electrophoresis, DNA was transferred onto a nylon membrane [Biodine, manufactured by Pall Corporation] according to the method of Southern et al. [J. Mol. Biol., 98, p 503 (1975)], and subjected to hybridization in the same manner as in the screening.

(7) Subcloning of positive clone

A phage DNA treated with BsiwI was subjected to agarose gel electrophoresis, and insert DNA was recovered using GENECLEAN II Kit. The DNA was end-blunted with Klenow enzyme, and the insert DNA was incorporated, using T4 ligase, into SmaI site of pBSIIKS(+) treated with BAP. The ligation solution was used to transform competent *Escherichia coli* DH5α. That is, competent *Escherichia coli* (0.3 ml) was added to the total amount of 7 µl of ligation solution, and the mixture was left standing on ice for several hours. The mixture was heat stimulated at 42° C. for 40 seconds and placed back on the ice. An LB medium (200 μl) was added, and the mixture was incubated at 37° C. for 30 minutes, then poured into an LB agar medium plate containing ampicillin, and incubated at 37° C. overnight. Single colonies were recovered and placed in 1.5 ml of LB medium, followed by shaking culture for 5 hours. pBSIIKS(+) DNA was recovered from centrifuged precipitate by alkali method [Molecular Cloning, A Laboratory Manual, second edition 1.25 (1989)].

(8) Determination of nucleotide sequence

The nucleotide sequence of DNase γ cDNA insert was determined from pBSIIKS(+) DNA obtained in (7) by a DNA sequencer (DSQ-1000, manufactured by Shimazu Corporation) using a TaKaRa Taq cycle sequence kit (for SIMAZU, manufactured by Takara Shuzo). As a result, all 16 positive clones were found to be encoding the whole length of DNase γ (Sequence List, SEQ ID NO: 2). The whole length of the cDNA clone was 1208 bp, containing an open reading frame consisting of 933 bp (SEQ ID NO: 2, nucleotide Nos. 12–944) inside, and encoded 310 amino acid residues (Sequence List, SEQ ID NO: 1). A comparison of amino acid sequence analysis of purified DNase γ protein N terminal revealed that the primary translation product of said DNase γ gene had a precursor peptide region consisting of 25 amino acid residues (SEQ ID NO: 1, amino acid Nos. 1–25) on the N terminal side. Accordingly, mature DNase γ protein consisted of 285 amino acid residues (SEQ ID NO: 1, amino acid Nos. 26–310) and the molecular weight of the protein assumed from said amino acid sequence was 33,027. This value matched well with the molecular weight of said protein by SDS-PAGE.

Example 4
Preparation of DNase γ antibody

Using, as antigens, two kinds of peptides (Table 5) synthesized based on the partial amino acid sequence of DNase γ of the present invention as determined in Example 3 (2), a polyclonal antibody against DNase γ was prepared.

TABLE 5

| peptide used as antigen |
| --- |
| KENHNAMDI |
| KEQYAFLYK |

A mixture of a complex wherein the above-mentioned two kinds of synthetic peptides were respectively crosslinked with Keyhole Limpets Hemocyanin (KLH, carrier protein) by maleimide method, and complete Freund adjuvant, was used as an antigen to immuize rabbits [Kbl:JW, 15 weeks old, male, weighing 3–3.5 kg (at initial immunization), two were used for each antigen] by subcutaneous injection (0.5 mg) on the back. Booster was given three times by 0.5 mg every 3 weeks from the initial immunization, and partial blood was taken 10 days from each booster. The antibody titer was determined, and 10 days after the final immunization (third booster), the whole blood was taken, from which anti-serum was obtained.

The antibody titer was determined by the following method.

The antigen was immobilized on a microtiter plate at a concentration of 10 μmg/ml. After blocking, partial blood (0, 31 and 52 days after initial immunization) of sensitized rabbit was diluted to $10^1$–$10^8$ and reacted with the antigen. After washing, anti-rabbit IgG-peroxydase-labeled secondary antibody was reacted, and after washing, antibody titer was determined by color development of substrate solution ABTS. As a result, the antibody titer was confirmed to increase with time in every case (Table 6).

Table 6 antibody titer test of anti-DNase γ serum
antigen used: KENHNAMDI

| | coated with antigen | | | blank | | |
| --- | --- | --- | --- | --- | --- | --- |
| | days after initial immunization | | | | | |
| dilution series | 0 | 31 | 52 | 0 | 31 | 52 |
| $10^1$ | 0.186 | 2.182 | 2.630 | 0.097 | 1.071 | 1.095 |
| $10^2$ | 0.095 | 0.807 | 1.461 | 0.081 | 0.182 | 0.118 |
| $10^3$ | 0.079 | 0.154 | 0.358 | 0.079 | 0.085 | 0.082 |
| $10^4$ | 0.078 | 0.097 | 0.151 | 0.075 | 0.077 | 0.080 |
| $10^5$ | 0.079 | 0.083 | 0.092 | 0.076 | 0.076 | 0.081 |
| $10^6$ | 0.078 | 0.082 | 0.084 | 0.077 | 0.078 | 0.078 |
| $10^7$ | 0.077 | 0.079 | 0.082 | 0.078 | 0.074 | 0.079 |
| $10^8$ | 0.076 | 0.076 | 0.081 | 0.077 | 0.077 | 0.077 | antigen used: KEQYAFLYK

| | coated with antigen | | | blank | | |
| --- | --- | --- | --- | --- | --- | --- |
| | days after initial immunization | | | | | |
| dilution series | 0 | 31 | 52 | 0 | 31 | 52 |
| $10^1$ | 0.175 | 2.445 | 2.537 | 0.112 | 0.116 | 0.121 |
| $10^2$ | 0.093 | 1.728 | 2.351 | 0.080 | 0.080 | 0.080 |
| $10^3$ | 0.092 | 0.663 | 0.928 | 0.078 | 0.076 | 0.074 |
| $10^4$ | 0.105 | 0.338 | 0.277 | 0.092 | 0.078 | 0.076 |
| $10^5$ | 0.105 | 0.241 | 0.165 | 0.081 | 0.079 | 0.079 |
| $10^6$ | 0.098 | 0.162 | 0.134 | 0.091 | 0.082 | 0.080 |
| $10^7$ | 0.114 | 0.131 | 0.126 | 0.103 | 0.086 | 0.080 |
| $10^8$ | 0.105 | 0.123 | 0.129 | 0.151 | 0.105 | 0.089 |

Industrial Applicability

The present invention provides novel DNases α, β and γ which catalyze the reaction of selectively cleaving the linker sites of chromatin DNA. The present invention also provides novel DNase r involved in apoptosis. The present invention further provides amino acid sequence of rat DNase γ, DNA encoding said amino acid sequence, nucleotide sequence of said DNA, recombinant vector containing said DNA, host cell transformed with said recombinant vector, production method of said DNase γ comprising culture of said host cell, and antibody against said DNase γ, precursor thereof and their fragments.

According to the DNase γ of the present invention, the molecular level elucidation of the control mechanism of carcinogenesis in the body by apoptosis, the control mechanism of autoimmune system, and the onset of AIDS is enabled, and the enzyme of the invention effectively contributes to the development of medications for the prevention, treatment and diagnosis of cancer, autoimmune diseases and viral infections. It is also considered that an antibody prepared from the DNase γ of the present invention is useful as a reagent for diagnosing the malignancy of cancer, in that higher malignancy causes lower activity of DNase γ in the cancer cells. Inhibitors and activating agents searched for using DNase γ activity as an index are advantageous in that they can be new "apoptosis controlling pharmaceutical products", and the gene of DNase γ is useful as an information and test sample for establishing apoptosis gene therapy for cancer (stimulation of apoptosis by enrichment of sense DNA) and autoimmune diseases (inhibition of apoptosis by anti-sense DNA).

In addition, the DNases α and β of the present invention increase upon viral infection to cleave viral DNA, and are useful for the development of therapeutic agents for viral infections. Moreover, an antibody prepared from the DNases α and β of the present invention is considered to be useful as a reagent for diagnosing viral infections and the like.

What is claimed is:

1. A purified antibody having an affinity for SEQ ID NO: 1, wherein SEQ ID NO: 1 is a deoxyribonuclease that is an endonuclease that selectively cleaves the linker sites of chromatin DNA and that has the following properties:

(i) localization: cell nucleus
   (ii) molecular weight:
      (a) 33,000 (SDS-PAGE)
      (b) 31,000 (gel filtration)
   (iii) optimal pH: 7.2
   (iv) divalent cation dependency: $Ca^{2+}/Mg^{2+}$, $Mn^{2+}$ dependent
   (v) inhibition by $Zn^{2+}$: $IC_{50}$=40 $\mu$M
   (vi) DNA cleavage mode: 3'-OH, 5'-P terminal forming type
   (vii) inhibition by G-actin: none.

* * * * *